United States Patent
Mirda et al.

(10) Patent No.: US 10,624,760 B2
(45) Date of Patent: Apr. 21, 2020

(54) SPINAL IMPLANT SYSTEM AND METHOD

(71) Applicant: Warsaw Orthopedic, Inc, Warsaw, IN (US)

(72) Inventors: James M. Mirda, Cordova, TN (US); Jonathan E. Blackwell, Lakeland, TN (US); Richard A. Hynes, Melbourne Beach, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 78 days.

(21) Appl. No.: 15/601,713

(22) Filed: May 22, 2017

(65) Prior Publication Data

US 2018/0333272 A1    Nov. 22, 2018

(51) Int. Cl.
*A61F 2/44* (2006.01)
*A61F 2/30* (2006.01)
(Continued)

(52) U.S. Cl.
CPC .......... *A61F 2/447* (2013.01); *A61F 2/30771* (2013.01); *A61F 2/4455* (2013.01); *A61F 2/4611* (2013.01); *A61B 6/487* (2013.01); *A61B 34/20* (2016.02); *A61B 2090/3937* (2016.02); *A61B 2090/3966* (2016.02); *A61F 2002/3008* (2013.01); *A61F 2002/30056* (2013.01); *A61F 2002/3078* (2013.01); *A61F 2002/3082* (2013.01); *A61F 2002/3092* (2013.01); *A61F 2002/3093* (2013.01); *A61F 2002/30143* (2013.01); *A61F 2002/30266* (2013.01); *A61F 2002/30281* (2013.01); *A61F 2002/30387* (2013.01); *A61F 2002/30398* (2013.01); *A61F 2002/30428* (2013.01); (Continued)

(58) Field of Classification Search
CPC .............. A61F 202/3008; A61F 2/4465; A61F 2/4455–447; A61F 2/30771; A61F 2002/4475
See application file for complete search history.

(56) References Cited

U.S. PATENT DOCUMENTS 5,443,515 A * 8/1995 Cohen ...................... A61F 2/44
                                                           606/247
5,728,159 A * 3/1998 Stroever .................. A61F 2/28
                                                           623/23.5
(Continued)

FOREIGN PATENT DOCUMENTS

| EP | 1384455 A1 | 1/2004 |
|---|---|---|
| EP | 2526901 A1 | 11/2012 |
| WO | WO 2007/038545 A1 | 4/2007 |

OTHER PUBLICATIONS

NPL1-Sustain, Sustain® & Sustain®-R, Large, 2016 http://www.globusmedical.com/portfolio/sustain-sustain-r-large/.
(Continued)

*Primary Examiner* — Jacqueline T Johanas

(57) ABSTRACT

An interbody implant includes an implant body extending between an anterior surface and a posterior surface. The implant body includes a first vertebral engaging surface and a second vertebral engaging surface. At least one of the vertebral engaging surfaces defines a cavity configured for disposal of bone growth detectable via medical imaging. Systems, spinal constructs, surgical instruments and methods are disclosed.

21 Claims, 17 Drawing Sheets

(51) Int. Cl.
  *A61F 2/46*  (2006.01)
  *A61B 6/00*  (2006.01)
  *A61B 90/00* (2016.01)
  *A61B 34/20* (2016.01)
(52) U.S. Cl.
  CPC ............ *A61F 2002/30538* (2013.01); *A61F 2002/30583* (2013.01); *A61F 2002/30784* (2013.01); *A61F 2002/30785* (2013.01); *A61F 2002/30836* (2013.01); *A61F 2002/30904* (2013.01); *A61F 2002/30922* (2013.01); *A61F 2002/30962* (2013.01); *A61F 2002/4475* (2013.01); *A61F 2002/4624* (2013.01); *A61F 2002/4628* (2013.01); *A61F 2002/4629* (2013.01)

(56) References Cited

U.S. PATENT DOCUMENTS

| | | | |
|---|---|---|---|
| 5,755,796 A | 5/1998 | Ibo et al. | |
| 6,025,538 A * | 2/2000 | Yaccarino, III | A61F 2/28 128/898 |
| 6,106,557 A | 8/2000 | Robioneck et al. | |
| 6,156,037 A | 12/2000 | LeHuec et al. | |
| 6,235,059 B1 | 5/2001 | Benezech et al. | |
| 6,402,785 B1 | 6/2002 | Zdeblick et al. | |
| 6,503,279 B1 | 1/2003 | Webb et al. | |
| 6,508,818 B2 | 1/2003 | Steiner et al. | |
| 6,579,318 B2 | 6/2003 | Varga et al. | |
| 6,843,805 B2 | 1/2005 | Webb et al. | |
| 6,974,480 B2 | 12/2005 | Messerli et al. | |
| 7,060,097 B2 * | 6/2006 | Fraser | A61B 17/025 623/17.11 |
| 7,169,183 B2 | 1/2007 | Liu et al. | |
| 7,204,852 B2 | 4/2007 | Marnay et al. | |
| 7,303,583 B1 | 12/2007 | Schar et al. | |
| 7,621,938 B2 | 11/2009 | Molz, IV | |
| 7,758,616 B2 | 7/2010 | LeHuec et al. | |
| 7,815,682 B1 * | 10/2010 | Peterson | A61F 2/4465 623/17.16 |
| 8,002,837 B2 | 8/2011 | Stream et al. | |
| 8,100,975 B2 | 1/2012 | Waugh et al. | |
| 8,105,381 B2 | 1/2012 | Marnay et al. | |
| 8,216,312 B2 | 7/2012 | Gray | |
| 8,357,200 B2 | 1/2013 | Adl | |
| 8,372,149 B2 | 2/2013 | Zdeblick et al. | |
| 8,435,300 B2 | 5/2013 | Messerli et al. | |
| 8,480,747 B2 | 7/2013 | Melkent et al. | |
| 8,579,978 B2 | 11/2013 | Marnay et al. | |
| 8,690,949 B2 | 4/2014 | Messerli et al. | |
| 8,801,785 B2 | 8/2014 | Brittan et al. | |
| 8,828,084 B2 | 9/2014 | Aflatoon | |
| 9,011,540 B1 * | 4/2015 | Castro | A61F 2/44 606/280 |
| 9,283,091 B2 * | 3/2016 | Melkent | A61F 2/4455 |
| 9,289,309 B2 | 3/2016 | Rhonda | |
| 9,730,802 B1 * | 8/2017 | Harvey | A61F 2/442 |
| 2002/0065560 A1 | 5/2002 | Varga et al. | |
| 2002/0095155 A1 | 7/2002 | Michelson | |
| 2003/0195632 A1 | 10/2003 | Foley et al. | |
| 2004/0172133 A1 | 9/2004 | Gerber et al. | |
| 2004/0186574 A1 | 9/2004 | Varga et al. | |
| 2005/0096748 A1 * | 5/2005 | Yoon | A61B 17/56 623/22.4 |
| 2005/0101960 A1 | 5/2005 | Fiere et al. | |
| 2005/0154460 A1 * | 7/2005 | Yundt | A61F 2/441 623/17.11 |
| 2005/0216082 A1 | 9/2005 | Wilson et al. | |
| 2006/0212119 A1 | 9/2006 | Varga et al. | |
| 2006/0241760 A1 | 10/2006 | Randall et al. | |
| 2006/0276900 A1 * | 12/2006 | Carpenter | A61F 2/442 623/17.15 |
| 2007/0073400 A1 | 3/2007 | Paul | |
| 2007/0118220 A1 | 5/2007 | Liu et al. | |
| 2008/0051890 A1 | 2/2008 | Waugh et al. | |
| 2008/0051902 A1 | 2/2008 | Dwyer | |
| 2008/0161925 A1 | 7/2008 | Brittan et al. | |
| 2008/0183294 A1 | 7/2008 | Adl | |
| 2008/0243252 A1 | 10/2008 | Hansen | |
| 2008/0288076 A1 * | 11/2008 | Soo | A61F 2/30771 623/17.16 |
| 2008/0300634 A1 | 12/2008 | Gray | |
| 2008/0312742 A1 | 12/2008 | Abernathie | |
| 2009/0204214 A1 * | 8/2009 | Fuji | A61F 2/30771 623/17.11 |
| 2009/0306779 A1 | 12/2009 | Ahn | |
| 2009/0326580 A1 | 12/2009 | Anderson et al. | |
| 2010/0070037 A1 | 3/2010 | Parry et al. | |
| 2011/0082550 A1 | 4/2011 | Yeh | |
| 2011/0202136 A1 | 8/2011 | Brittam et al. | |
| 2012/0143336 A1 | 6/2012 | Aflatoon et al. | |
| 2012/0245690 A1 | 9/2012 | Cowan, Jr. et al. | |
| 2012/0277865 A1 | 11/2012 | Trieu et al. | |
| 2013/0053894 A1 | 2/2013 | Gamache et al. | |
| 2013/0060337 A1 | 3/2013 | Petersheim et al. | |
| 2013/0166027 A1 | 6/2013 | Bellas | |
| 2013/0218276 A1 | 8/2013 | Fiechter et al. | |
| 2013/0231749 A1 | 9/2013 | Armstrong et al. | |
| 2013/0238095 A1 | 9/2013 | Pavento et al. | |
| 2013/0253655 A1 | 9/2013 | Blain | |
| 2013/0345813 A1 | 12/2013 | Frank et al. | |
| 2014/0114415 A1 | 4/2014 | Tyber | |
| 2014/0121777 A1 * | 5/2014 | Rosen | A61F 2/442 623/17.16 |
| 2014/0172103 A1 | 6/2014 | O'Neil et al. | |
| 2015/0018958 A1 * | 1/2015 | Ullrich, Jr. | A61F 2/3094 623/17.16 |
| 2015/0025635 A1 | 1/2015 | Laubert | |
| 2015/0032220 A1 | 1/2015 | Tyber et al. | |
| 2015/0100129 A1 | 4/2015 | Waugh et al. | |
| 2015/0305889 A1 | 10/2015 | Marnay et al. | |
| 2016/0113773 A1 * | 4/2016 | Ganem | A61F 2/30965 623/17.16 |
| 2016/0193057 A1 | 7/2016 | Rhoda | |
| 2016/0213487 A1 * | 7/2016 | Wilson | A61B 17/7059 |
| 2016/0213488 A1 * | 7/2016 | Moore | A61F 2/4455 |
| 2016/0278934 A1 * | 9/2016 | Mermuys | A61F 2/442 |
| 2016/0324653 A1 * | 11/2016 | Flickinger | A61F 2/2846 |
| 2017/0000623 A1 | 1/2017 | Arramon et al. | |
| 2017/0079805 A1 * | 3/2017 | Costabile | A61F 2/447 |
| 2018/0256363 A1 * | 9/2018 | Moon | A61F 2/4465 |
| 2018/0289502 A1 * | 10/2018 | Zappacosta | A61B 17/7059 |
| 2018/0303624 A1 * | 10/2018 | Shoshtaev | A61F 2/4465 |

OTHER PUBLICATIONS

European Search Report for EP18171198.7 date of completion is Sep. 27, 2018 (9 pages).

* cited by examiner

SPINAL IMPLANT SYSTEM AND METHOD

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as degenerative disc disease, disc herniation, spondylolisthesis, stenosis, osteoporosis, tumor, scoliosis, kyphosis and other curvature abnormalities, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, microdiscectomy, corpectomy, decompression, laminectomy, laminotomy, foraminotomy, facetectomy and implantable prosthetics. As part of these surgical treatments, spinal constructs, such as, for example, bone fasteners, spinal rods and interbody devices can be used to provide stability to a treated region. During surgical treatment, surgical instruments can be used to deliver components of the spinal constructs to a surgical site. For example, interbody implants can be delivered to the surgical site for fixation with bone to immobilize a joint. Such interbody implants can include bone growth promoting material to enhance fixation of the interbody implants with the bone. This disclosure describes an improvement over these prior technologies.

SUMMARY

In one embodiment, an interbody implant is provided. The interbody implant includes an implant body extending between an anterior surface and a posterior surface. The implant body includes a first vertebral engaging surface and a second vertebral engaging surface. At least one of the vertebral engaging surfaces defines a cavity configured for disposal of bone growth detectable via medical imaging. In some embodiments, systems, spinal constructs, surgical instruments and methods are provided.

In one embodiment, a method for treating a spine is provided. The method comprises the steps of: connecting a surgical instrument with an implant body adjacent a cavity of the interbody implant, the implant body including an opening extending through a thickness of the implant body and a recess; disposing the implant body between a first vertebral surface and a second vertebral surface of a subject body; manipulating the implant body between a non-aligned orientation such that visualization of the opening is obstructed by a surface of the implant body that prevents radiographic visualization of the opening and an aligned orientation such that the surface is oriented to allow radiographic visualization of the opening; and manipulating the implant body such that recess is detectable to indicate orthogonal alignment of the implant body with the vertebral surfaces.

BRIEF DESCRIPTION OF THE DRAWINGS

The present disclosure will become more readily apparent from the specific description accompanied by the following drawings, in which.

DETAILED DESCRIPTION

Figure 1:
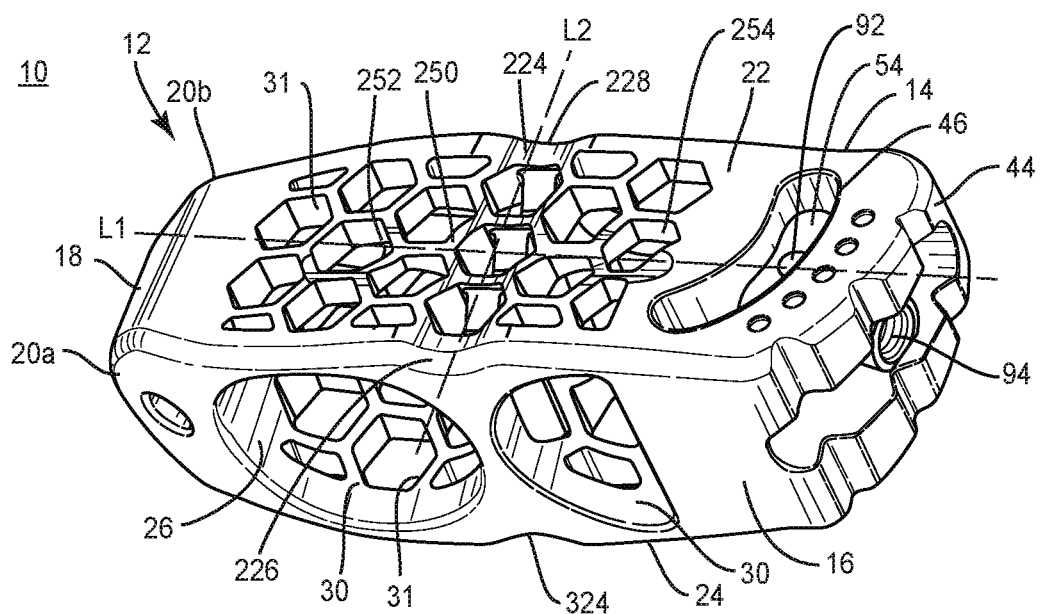
FIG. 1 is a perspective view of components of one embodiment of a surgical system in accordance with the principles of the present disclosure.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure are employed with a spinal joint and fusion, for example, with a cervical, thoracic, lumbar and/or sacral region of a spine.

In some embodiments, the present surgical system includes an interbody implant. In some embodiments, the surgical system includes an interbody implant having one or more troughs or through features. In some embodiments, the troughs are configured to assess fusion and/or orthogonal alignment of the interbody implant with tissue. In some embodiments, the troughs or through features are configured to provide visualization of bone growth adjacent to an endplate of vertebrae. In some embodiments, the troughs provide indicia, for example, radiographically, which indicates bone growth. In some embodiments, the interbody implant does not include a trough or through feature. In some embodiments, the interbody implant includes a surface having micro-texture to avoid subsidence with tissue.

In some embodiments, the surgical system includes an interbody implant that can be aligned orthogonally with tissue. For example, the interbody implant can define a longitudinal axis such that the interbody implant is manipulable to dispose the longitudinal axis orthogonal to a bi-lateral axis of vertebrae. For example, the interbody implant can define a transverse axis such that the interbody implant is manipulable to dispose the transverse axis parallel or co-axial to the bi-lateral axis. In some embodiments, the surgical system includes an interbody implant having one or more openings that provide indicia of disposal of the interbody implant in a selected alignment with tissue.

In some embodiments, the interbody implant includes an elongated opening extending through a thickness thereof such that in an orthogonal alignment orientation of the interbody implant with tissue the opening is radiographically detectable and in a non-aligned orientation is non-detectable. In some embodiments, the orthogonal alignment and non-aligned orientations of the opening are detectable for visualization radiographically in an AP view of vertebrae. In some embodiments, the orthogonal alignment and non-aligned orientations of the opening are detectable for visualization radiographically in a lateral view of vertebrae. In some embodiments, the interbody implant includes an elongated recess extending along an outer surface thereof such that in an orthogonal alignment orientation of the interbody implant with tissue the recess is radiographically detectable and in a non-aligned orientation is non-detectable. In some embodiments, the orthogonal alignment and non-aligned orientations of the recess are detectable for visualization radiographically in a lateral view of vertebrae.

In some embodiments, the surgical system includes an interbody implant having one or more troughs that comprise a void. In some embodiments, the interbody implant includes an arcuate surface that defines the void. In some embodiments, the interbody implant includes one or more troughs disposed parallel to vertebral endplates and/or disposed at an angular orientation that matches lordosis. In some embodiments, the interbody implant includes one or more troughs disposed parallel to vertebral engaging surfaces of the implant and/or vertebral endplates, parallel to an axial or transverse plane of vertebrae, at a selected angular orientation relative to the vertebral engaging surfaces and/or at a selected angular orientation relative to vertebral endplates or the axial or transverse planes, or at an angular orientation that matches lordosis. In some embodiments, the interbody implant includes one or more troughs disposed parallel to an axial plane of vertebrae. In some embodiments, the interbody implant includes one or more troughs having a posterior portion disposed parallel to vertebral engaging surfaces, vertebral endplates and/or at an angular orientation that matches lordosis, and an anterior portion disposed parallel to an axial plane or transverse plane of vertebrae.

In some embodiments, the surgical system includes an interbody implant having one or more troughs disposed with a superior surface thereof. In some embodiments, the surgical system includes an interbody implant having one or more troughs disposed with an inferior surface thereof. In some embodiments, the trough has a linear configuration and is disposed in an anterior to posterior orientation on one or more endplate engaging surfaces of the interbody implant. In some embodiments, the trough has a linear configuration and is disposed in a lateral orientation on one or more endplate engaging surfaces of the interbody implant. In some embodiments, the trough has a linear configuration and is disposed in an oblique orientation relative to a sagittal or coronal body plane on one or more endplate engaging surfaces of the interbody implant. In some embodiments, the trough is disposed with a midline of the interbody implant. In some embodiments, the trough is disposed offset from a midline of the interbody implant.

In some embodiments, the surgical system includes an interbody implant having a trough disposed with a superior surface and a trough disposed with an inferior surface, the troughs being disposed in an anterior to posterior orientation. In some embodiments, the surgical system includes an interbody implant having a trough disposed with a superior surface and a trough disposed with an inferior surface, the troughs being disposed in a lateral orientation. In some embodiments, the trough is 5 millimeters (mm) wide and 1 mm deep. In some embodiments, the superior surface of the interbody implant that includes the trough has a 3.0 mm radius edge that defines the trough. In some embodiments, the trough is 4.5 mm wide and has a depth in a range of 0.6 to 0.8 mm.

In some embodiments, the interbody implant includes an interbody cage. In some embodiments, the surgical system includes a plate that is affixed to an interbody implant and a superior vertebral body and/or an inferior vertebral body adjacent an interbody space of vertebrae. In some embodiments, the surgical system includes an interbody implant connected with a plate, locks and/or insertion mechanisms. In some embodiments, the surgical system includes one or more radiographic markers selectively disposed with one or more components of the surgical system. In some embodiments, the surgical system includes a hyper-lordotic interbody implant configured to achieve lordosis of vertebrae in a range of 0 to 30 angular degrees.

In some embodiments, the surgical system is used with medical imaging, such as, for example, fluoroscopy, CT, MRI or other imaging techniques, which may comprise microsurgical and image guided technologies, such as, for example, a surgical navigation system employing emitters and sensors, which may be employed to track the components of the surgical system. See, for example, the surgical navigation components and their use, as described in U.S. Pat. Nos. 6,021,343, 6,725,080 and 6,7969,88, the entire contents of each of these references being incorporated by reference herein. In some embodiments, one or all of the components of the surgical system are disposable, peel-pack, pre-packed sterile devices. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-14, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as hydroxyapatite (HA), corraline HA, biphasic calcium phosphate, tricalcium phosphate, or fluorapatite, tri-calcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure, including percutaneous techniques, and mini-open surgical techniques to deliver and introduce instrumentation and/or an implant, such as, for example, an interbody implant, at a surgical site of a patient, which includes, for example, a spine having vertebrae V (FIGS. 15-18). In some embodiments, a surgical pathway P to a surgical site is formed via various procedures, such as, for example, an oblique lateral interbody fusion (OLIF), a direct lateral interbody fusion (DLIF), a posterior lumbar interbody fusion (PLIF), an anterior lumbar interbody fusion (ALIF), an oblique lateral interbody fusion at L2-L5 (OLIF25), an oblique lateral interbody fusion at L5-S1 (OLIF51), a trans-psoas, an anterior, a lateral, an oblique, a retroperitoneal, or an ante-psoas procedures. In some embodiments, spinal implant system 10 is employed with a Smith-Petersen osteotomy, a Ponte-type osteotomy, a chevron-type osteotomy, a partial facet joint resection, a complete facet joint resection for removal of posterior-most bony structures, as described herein. In some embodiments, surgical system 10 can be employed with various surgical approaches to the spine, including anterior, posterior, posterior mid-line, direct lateral, postero-lateral, and/or antero-lateral approaches. In some embodiments, these approaches may be done in isolation, sequentially or simultaneously. In some embodiments, the implant can include spinal constructs, such as, for example, bone fasteners, spinal rods, connectors and/or plates.

Figure 2:
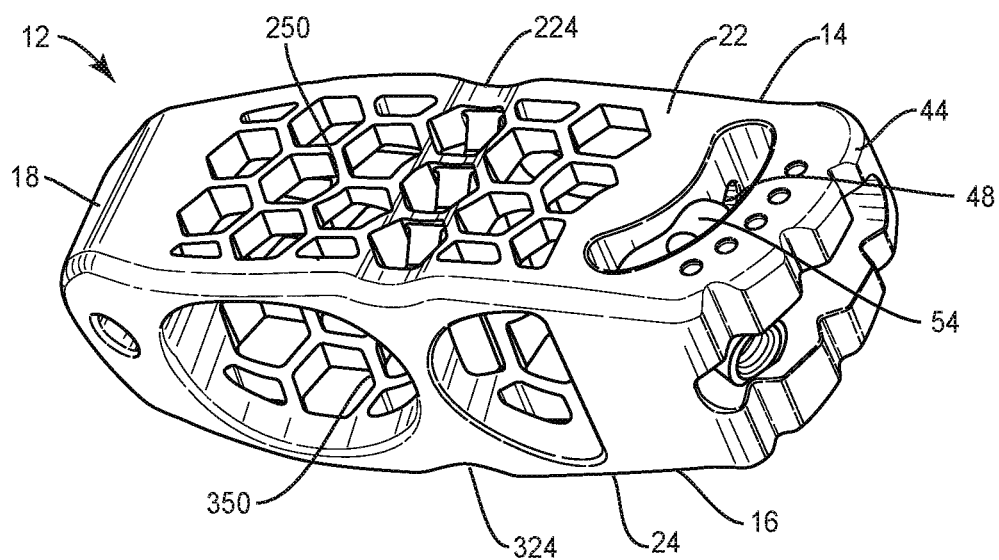
FIG. 2 is a perspective view of the components shown in FIG. 1.
Figure 3:
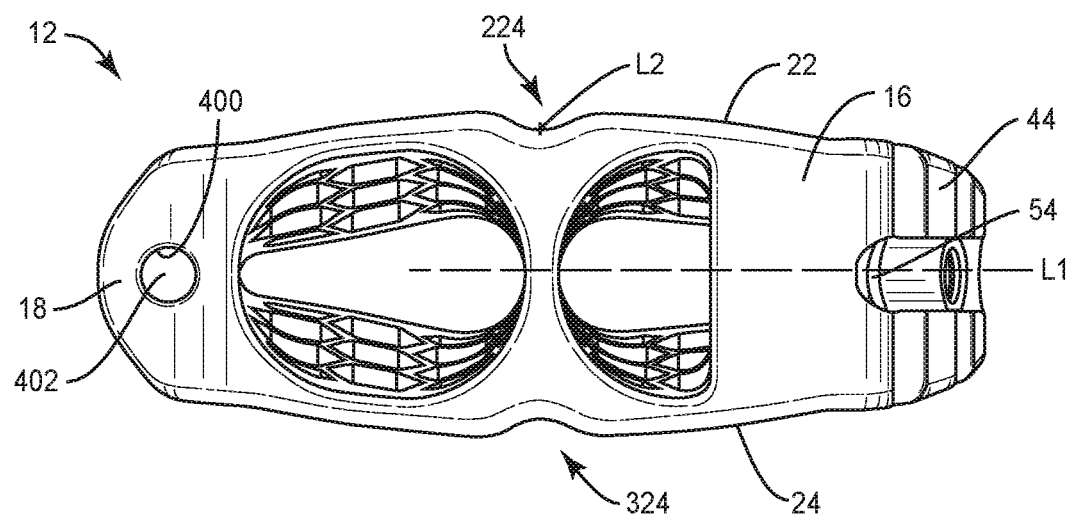
FIG. 3 is a front view of the components shown in FIG. 1.

Spinal implant system 10 includes an implant body, such as, for example, an interbody cage 12, as shown in FIGS. 1-3. Cage 12 extends between a posterior surface 14 and an anterior surface 16 and defines an axis L1. Posterior surface 14 is configured to face a posterior side of a subject body and be disposed adjacent a posterior portion of vertebrae, such as, for example, a posterior portion P1 of one or more intervertebral spaces of vertebrae V (FIGS. 15-18). Anterior surface 16 is configured to face an anterior side of subject body and be disposed adjacent an anterior portion of vertebrae, such as, for example an anterior portion A1 of one or more intervertebral spaces of vertebrae V.

In some embodiments, cage 12 includes a convex distal end, such as, for example, a bullet nose 18 to facilitate insertion by a surgeon. In some embodiments, cage 12 may include chamfers, such as, for example, cut outs 20a, 20b disposed on bullet nose 18 such that cage 12 may be placed in an intervertebral space to avoid impinging on various structures in or adjacent vertebral tissue, such as, for example, a spinal foramina.

Figure 16:
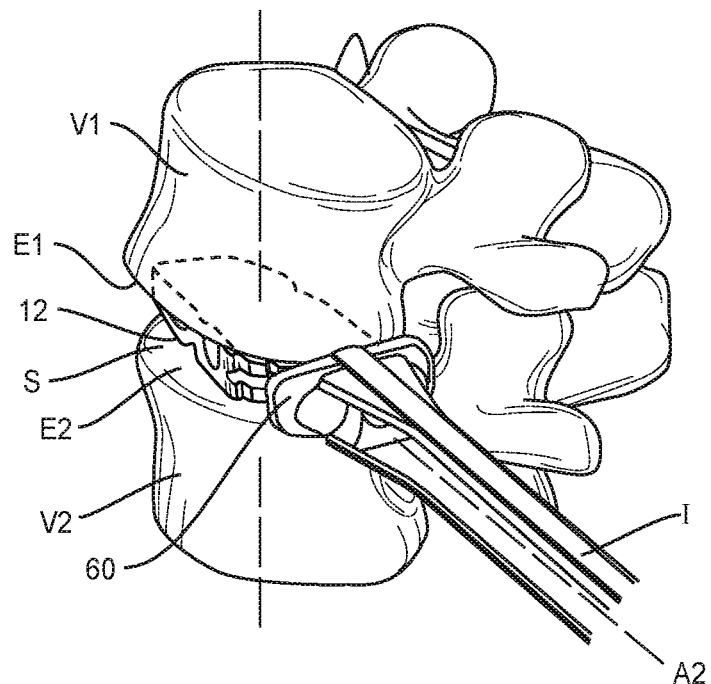
FIG. 16 is a perspective view of the components and vertebrae shown in FIG. 15.
Figure 17:
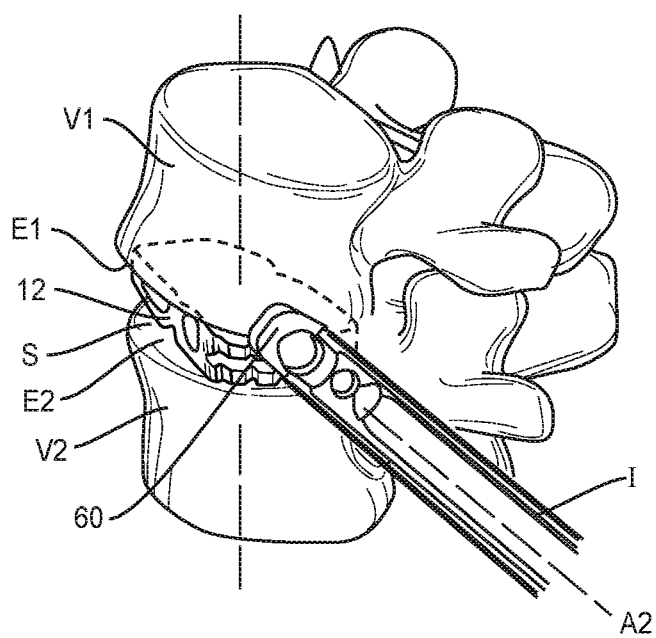
FIG. 17 is a perspective view of the components and vertebrae shown in FIG. 15.

Cage 12 includes a vertebral engaging surface 22 and a vertebral engaging surface 24. Surface 22 may be substantially planar and configured to engage endplate tissue of a vertebral body, such as, for example, an endplate E1 of a vertebral level V1 (FIG. 16). Surface 24 may be substantially planar and configured to engage endplate tissue of a vertebral body, such as, for example, an endplate E2 of a vertebral level V2 (FIG. 16). In some embodiments, surface 22 and/or surface 24 may be rough, textured, porous, semi-porous, dimpled, knurled, toothed, grooved and/or polished to facilitate engagement with tissue. In some embodiments, one or more surfaces of cage 12 includes micro-texture to avoid subsidence with tissue. In some embodiments, surface 22 and/or surface 24 may comprise a cephalad and/or a caudal oriented surface.

In some embodiments, surface 22 and/or surface 24 may be partially convex along axis L1 and/or at least partially convex in a direction substantially perpendicular to an axis L2 (i.e., from surface 16 to surface 14). In some embodiments, surface 22 and/or surface 24 may be angled along axis L1 or angled perpendicular to axis L1 such that anterior surface 16 is taller than posterior surface 14 such that cage 12 may be capable of creating and/or augmenting lateral or lordotic curvature in a spine when implanted. In some embodiments, surface 22 and surface 24 are disposed at a relative angular orientation to include a hyper-lordotic configuration to correct lumbar lordosis in situations where a natural curve of a lumbar region of the back is accentuated. In some embodiments, surface 22 and surface 24 are disposed at a relative angular orientation in a range of greater than 12 degrees.

In some embodiments, vertebral tissue includes intervertebral tissue, endplate surfaces and/or cortical bone. In some embodiments, surface 22 and/or surface 24 may be coated with materials suitable for facilitating or encouraging bony ongrowth or fusion including but not limited to titanium and HA coatings. In some embodiments, a titanium coating is applied to surface 22 and/or surface 24 in a porous layer using plasma spray technology.

Surface 22 defines a cavity, such as, for example, a groove 224. Groove 224 is configured to provide indicia of bone growth, as described herein. In some embodiments, groove 224 includes a trough configuration for disposal of bone growth. Groove 224 extends between an end 226 and an end 228. End 226 is disposed adjacent anterior surface 16 and end 228 is disposed adjacent posterior surface 14 such that groove 224 extends in an anterior to posterior orientation along surface 22. In some embodiments, groove 224 extends along only a portion or the entire surface 22 between surfaces 14, 16.

The portion of surface 22 that defines groove 224 comprises indicia that facilitates detecting bone growth in and/or through groove 224 and surface 22 via medical imaging, as described herein. The indicia is configured to facilitate visualization of a progression of bone growth into groove 224, for example, during fusion. In some embodiments, groove 224 includes a linear configuration disposed along surface 22. In some embodiments, all or only a portion of groove 224 may extend along surface 22 in alternate orientations, such as, for example, arcuate, undulating, irregular, uniform, non-uniform, offset, staggered, and/or tapered. In some embodiments, groove 224 can include various cross sections, such as, for example, oval, oblong, triangular, square, polygonal, irregular, uniform, non-uniform, variable and/or tapered. In some embodiments, all or only a portion of surface 22 may have alternate surface configurations, such as, for example, rough, arcuate, undulating, mesh, porous, semi-porous, dimpled and/or textured. In some embodiments, groove 224 includes an arcuate surface configuration configured to facilitate bone growth.

Figure 8:
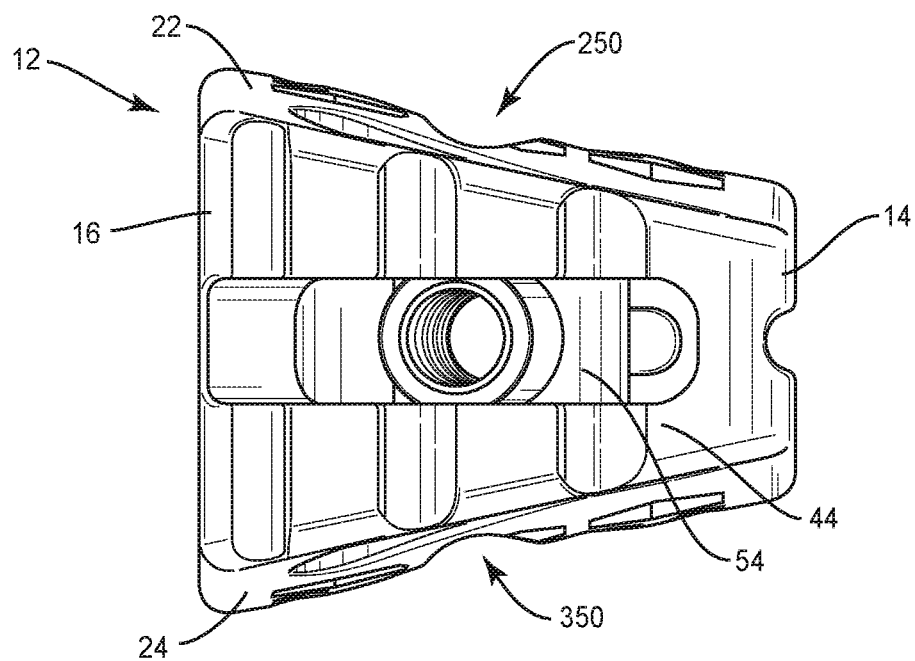
FIG. 8 is a side view of the components shown in FIG. 1.

Surface 22 defines a groove 250, as shown in FIG. 8, similar to groove 224 described herein. Groove 250 extends between an end 252 and an end 254, and in a medial to lateral orientation along surface 22 and axis L1. Groove 250 extends transverse to groove 224 to intersect and communicate therewith. The portion of surface 22 that defines groove 250 comprises indicia that facilitates detecting bone growth in and/or through groove 250 and surface 22 via medical imaging, as described herein. The indicia is configured to facilitate visualization of a progression of bone growth into groove 250, for example, during fusion. In some embodiments, groove 250 may be disposed at alternate orientations, relative to groove 224, such as, for example, perpendicular and/or other angular orientations, such as acute or obtuse, and/or may be separate, spaced apart, offset or staggered.

Surface 24 defines a groove 324, as shown in FIG. 3, similar to groove 224 described herein. Groove 324 extends in an anterior to posterior orientation along surface 24. The portion of surface 24 that defines groove 324 comprises indicia that facilitates detecting bone growth in and/or through groove 324 and surface 24 via medical imaging, as described herein. The indicia is configured to facilitate visualization of a progression of bone growth into groove 324, for example, during fusion. In some embodiments, groove 324 may be disposed at alternate orientations, relative to groove 224 and/or groove 250, as described herein.

Surface 22 defines a groove 350, as shown in FIG. 8, similar to groove 224 described herein. Groove 350 extends in a medial to lateral orientation along surface 24 and axis L1. Groove 350 extends transverse to groove 324 to intersect and communicate therewith. The portion of surface 24 that defines groove 350 comprises indicia that facilitates detecting bone growth in and/or through groove 350 and surface 24 via medical imaging, as described herein. The indicia is configured to facilitate visualization of a progression of bone growth into groove 350, for example, during fusion. In some embodiments, groove 350 may be disposed at alternate orientations, relative to groove 224, groove 250 and/or groove 324, as described herein.

Figure 18:
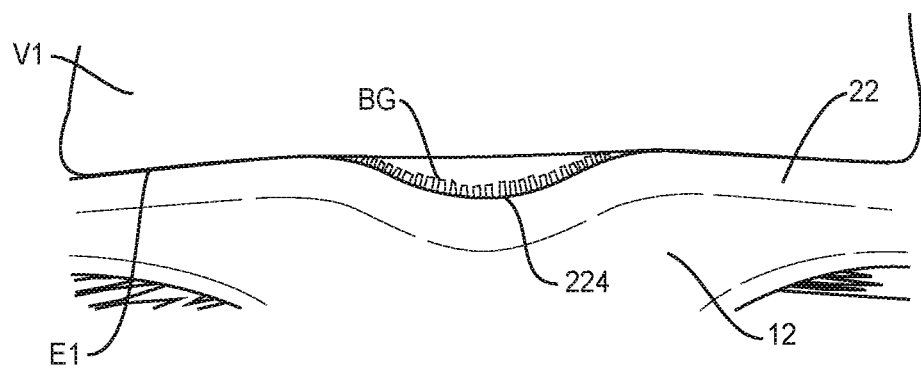
FIG. 18 is a plan view of components of one embodiment of a surgical system in accordance with the principles of the present disclosure disposed with vertebrae.

In some embodiments, the indicia of surfaces 22, 24 that defines grooves 224, 250, 324 and/or 350 comprise radiographic visual indicia. In some embodiments, the indicia includes radio-opaque material applied to surface 22 and/or surface 24 in a predetermined pattern. In some embodiments, the indicia may include visual indicia, one or more viewing portals, tactile indicia, and/or one or more components having markers for identification with medical imaging, as described herein. During fusion, bone grows into and around cage 12 to fuse the treated vertebrae. Grooves 224, 250, 324, 350 are configured to provide a space of cage 12 for bone growth to develop and such bone growth being identified and/or detectable radiographically for assessment. The indicia disposed with surfaces 22, 24 of grooves 224, 250, 324, 350 facilitates providing visual data by medical imaging of a rate, amount and or progression of bone growth during fusion within, along or through grooves 224, 250, 324, 350 (FIG. 18).

Figure 4:
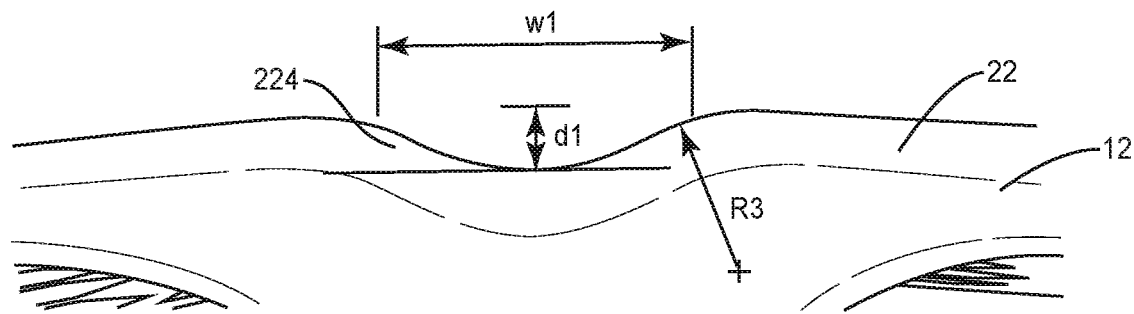
FIG. 4 is a break away view of the components shown in FIG. 3.
Figure 5:
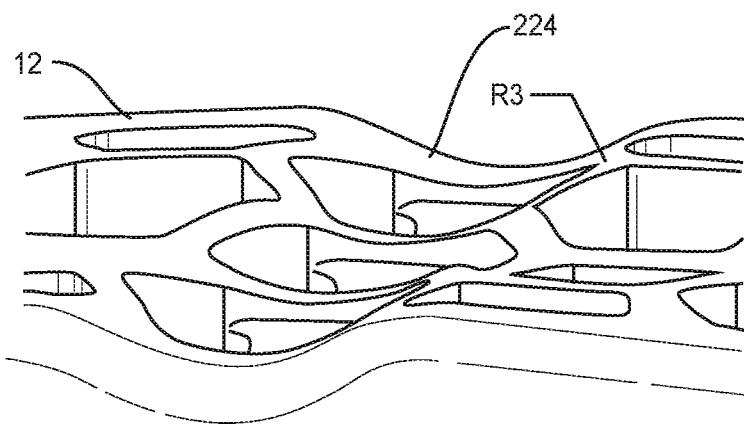
FIG. 5 is a break away view of the components shown in FIG. 1.
Figure 6:
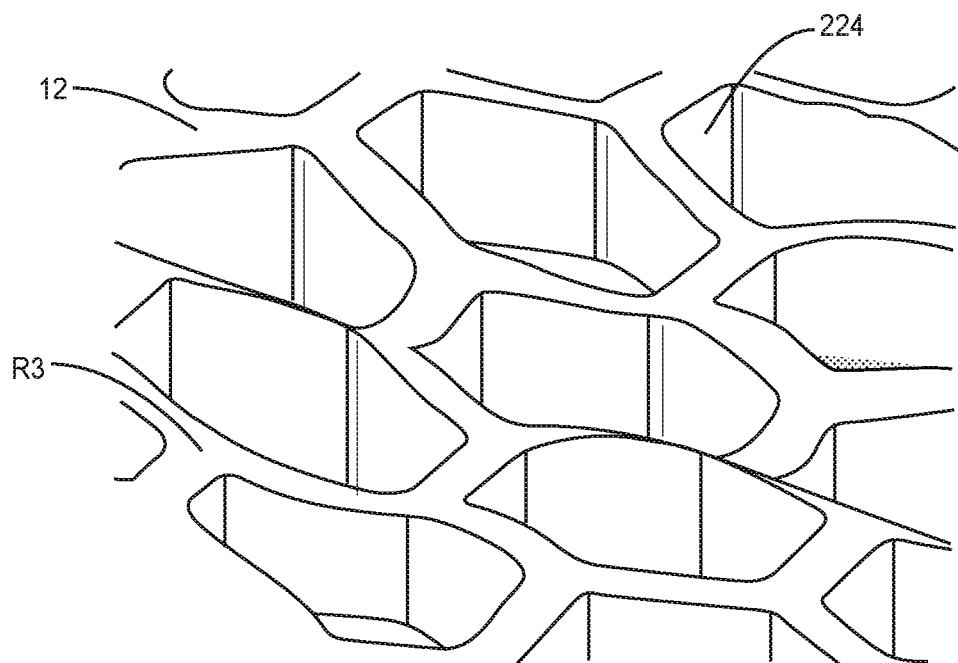
FIG. 6 is a break away view of the components shown in FIG. 5.
Figure 7:
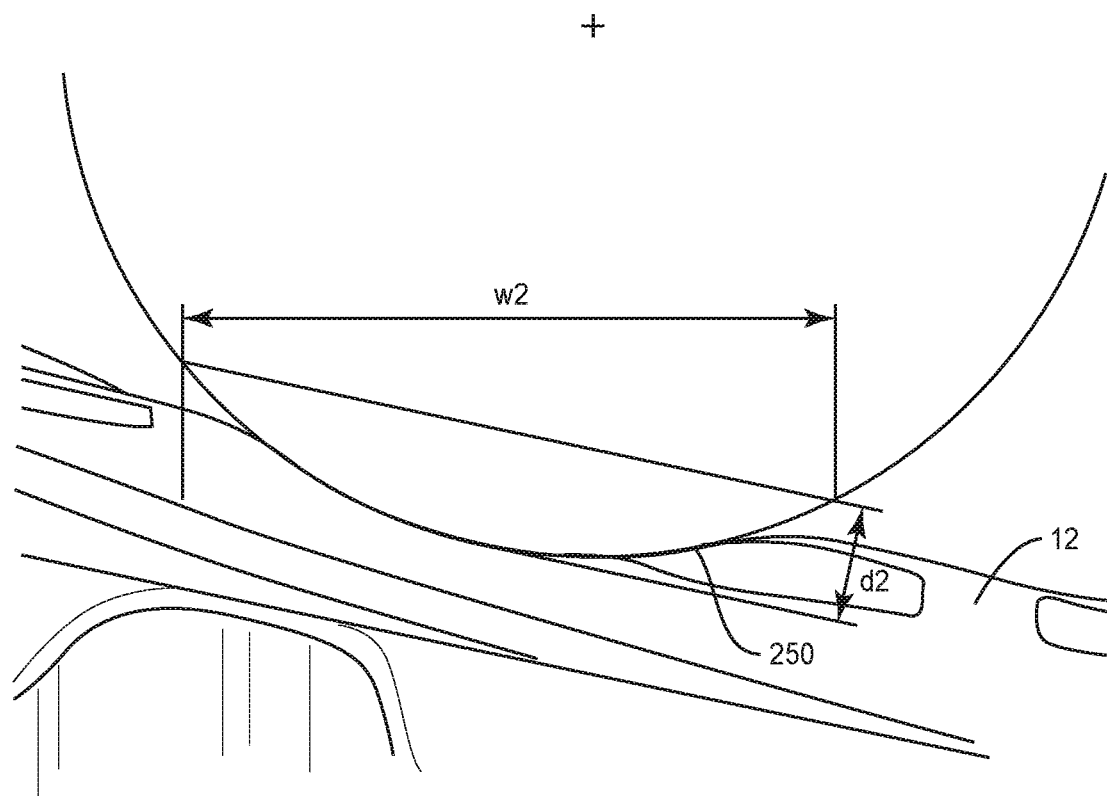
FIG. 7 is a break away view of the components shown in FIG. 1.

In some embodiments, grooves 224, 324 include a width w1 of approximately 5.0 mm, as shown in FIG. 4. In some embodiments, grooves 224, 324 include a depth d1 wide of approximately 1.0 mm. In some embodiments, grooves 224, 324 include edges having a radius R3 of 3.0 mm, as shown in FIGS. 5 and 6. In some embodiments, grooves 250, 350 include a width w2 of approximately 4.5 mm, as shown in FIG. 7. In some embodiments, grooves 250, 350 include a depth d2 in a range of 0.6 mm to 0.8 mm. In some embodiments, depth d2 of grooves 250, 350 increases as a height of cage 12 increases. In some embodiments, grooves 250, 350 include edges having a radius of 3.0 mm.

In some embodiments, cage 12 includes a plurality of grooves 224 and/or grooves 250, as described herein, disposed along axis L1, axis L2, a portion of surface 22, all of surface 22 or an entire area of surface 22 to provide indicia, as described herein, of bone growth continuity at one or more selected locations of surface 22. In some embodiments, cage 12 includes a plurality of grooves 224 and/or grooves 250 that are spaced apart. In some embodiments, cage 12 includes a plurality of grooves 224 and/or grooves 250 that are side by side, contiguous or adjacent. In some embodiments, cage 12 includes a plurality of grooves 224 and/or grooves 250 that are disposed in a relatively parallel orientation. In some embodiments, cage 12 includes a plurality of grooves 224 and/or grooves 250 that are disposed in a relatively transverse orientation and/or may intersect.

In some embodiments, cage 12 includes a plurality of grooves 324 and/or grooves 350, as described herein, disposed along axis L1, axis L2, a portion of surface 24, all of surface 24 or an entire area of surface 24 to provide indicia, as described herein, of bone growth continuity at one or more selected locations of surface 24. In some embodiments, cage 12 includes a plurality of grooves 324 and/or grooves 350 that are spaced apart. In some embodiments, cage 12 includes a plurality of grooves 324 and/or grooves 350 that are side by side, contiguous or adjacent. In some embodiments, cage 12 includes a plurality of grooves 324 and/or grooves 350 that are disposed in a relatively parallel orientation. In some embodiments, cage 12 includes a plurality of grooves 324 and/or grooves 350 that are disposed in a relatively transverse orientation and/or may intersect.

Figure 9:
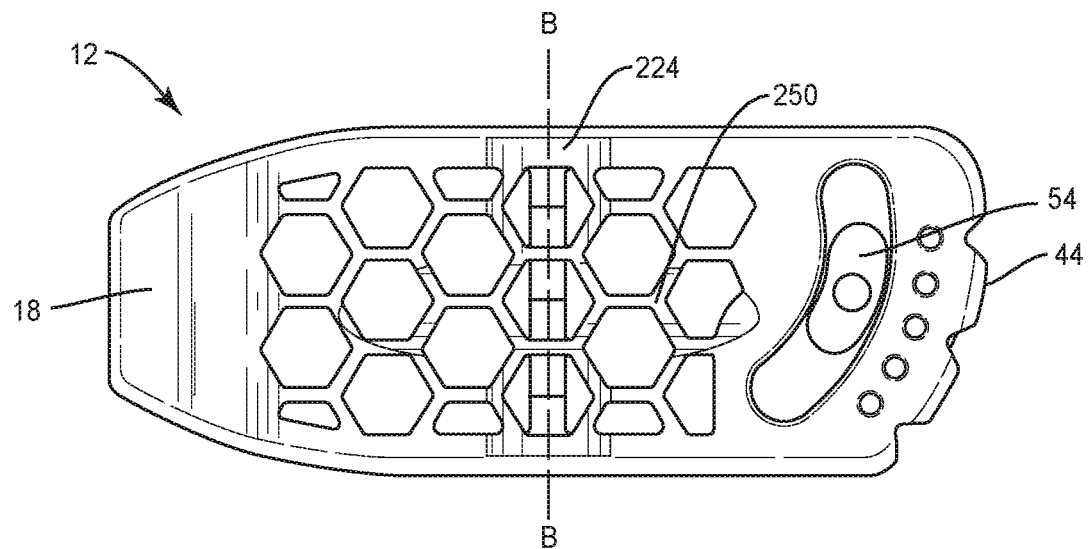
FIG. 9 is a plan view of the components shown in FIG. 1.
Figure 10:
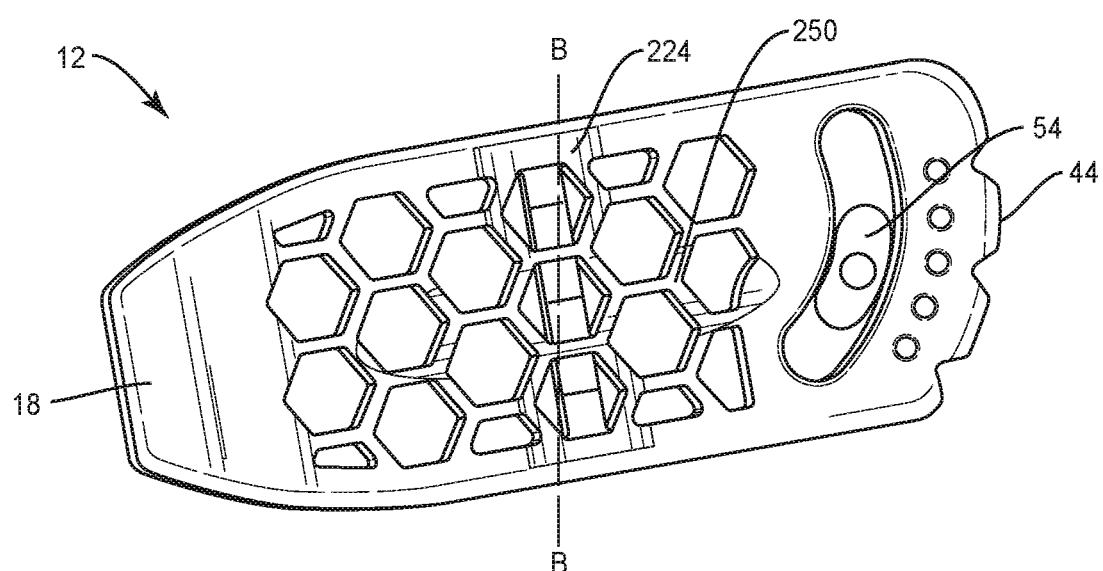
FIG. 10 is a plan view of the components shown in FIG. 9.
Figure 11:
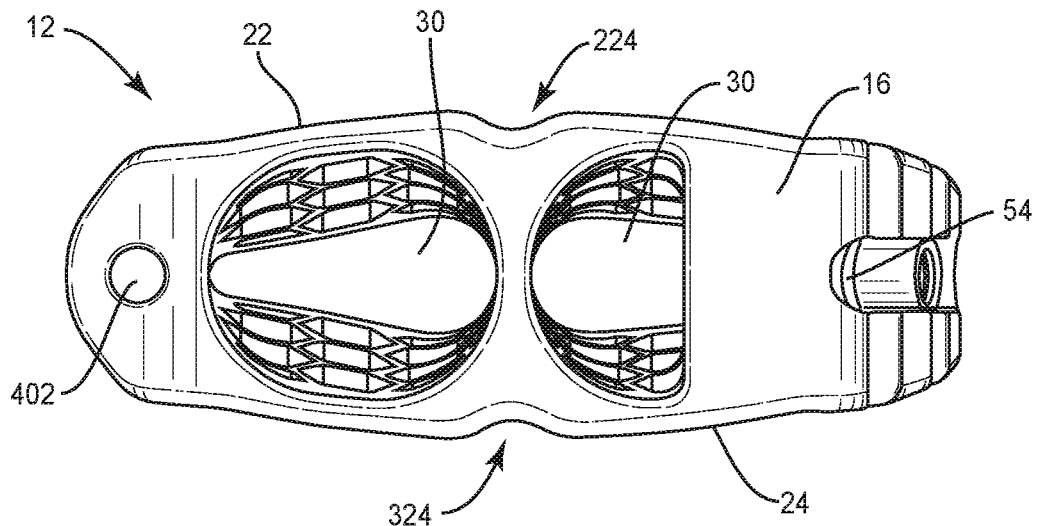
FIG. 11 is a front view of components of the components shown in FIG. 1.
Figure 12:
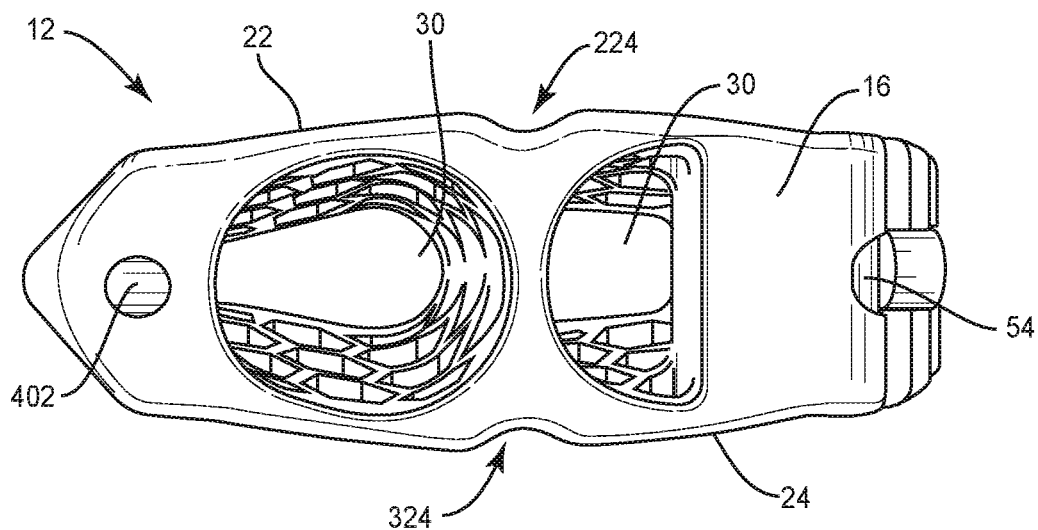
FIG. 12 is a perspective view of the components shown in FIG. 11.

Cage 12 includes a surface 400 that defines an opening 402, as shown in FIGS. 11 and 12. In some embodiments, opening 402 extends through a thickness of cage 12, as shown in FIG. 11. Surface 400 includes indicia, similar to that described herein, for visualization by medical imaging, as described herein. The indicia is radiographically detectable to indicate orthogonal alignment of cage 12 relative to a bi-lateral axis B of vertebrae, endplates and/or an intervertebral disc space, such that opening 402 is disposable between a non-aligned orientation, as shown in FIG. 10, and an aligned orientation, as shown in FIG. 9. For example, when cage 12 is disposed relative to tissue in the non-aligned orientation, visualization of opening 402 is obstructed such that surface 400 is oriented to prevent radiographic visualization of opening 402 through the body of cage 12, as shown in FIG. 12. When cage 12 is rotated relative to tissue to the aligned orientation, surface 400 is oriented to allow radiographic visualization of opening 402 through the body of cage 12, as shown in FIG. 11. In some embodiments, opening 402 is disposed in an anterior to posterior orientation. In some embodiments, opening 402 is disposed in a medial to lateral orientation.

Figure 13:
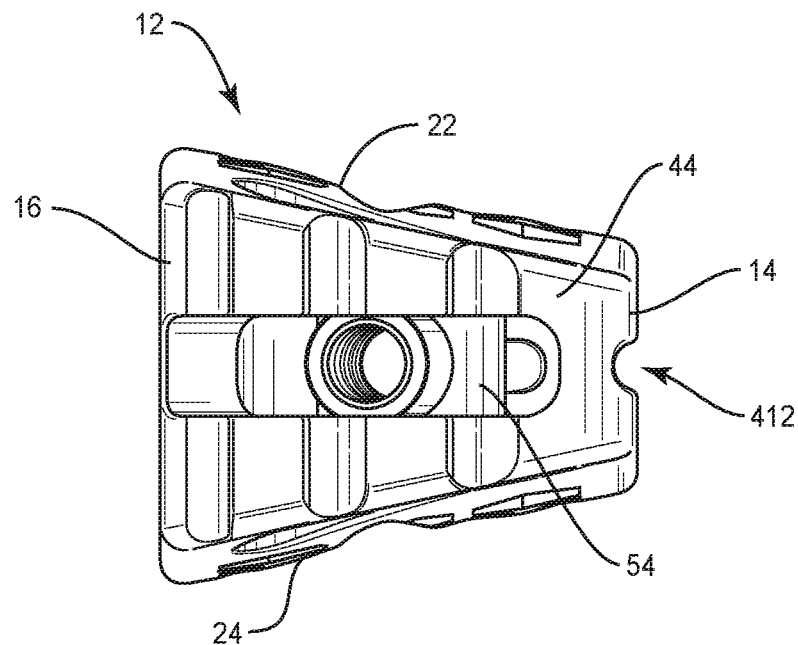
FIG. 13 is a side view of the components shown in FIG. 1.
Figure 14:
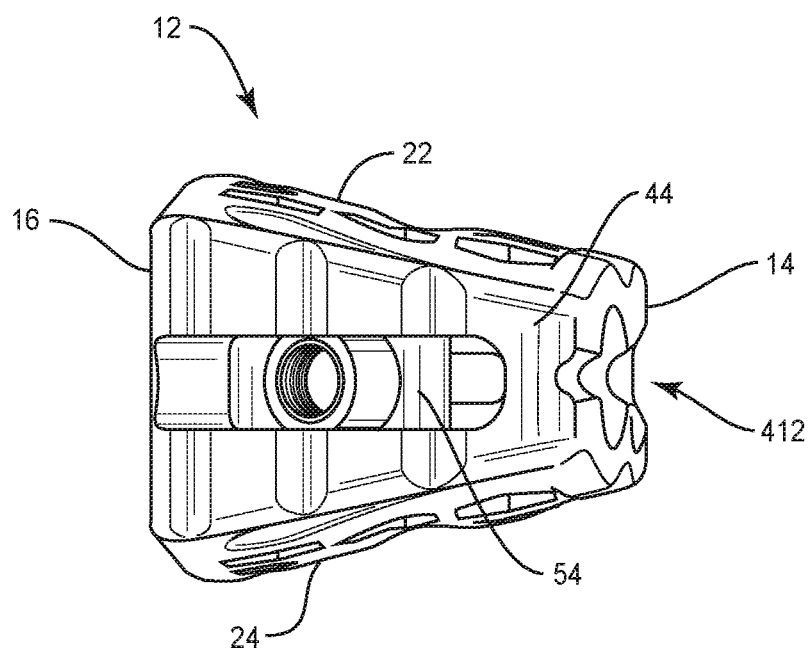
FIG. 14 is a perspective view of the components shown in FIG. 1.

In some embodiments, surface 14 defines a recess 412, as shown in FIGS. 13 and 14. Recess 412 extends between nose 18 and a surface 44, as described herein. Surface 14 includes indicia, similar to the indicia described herein, for visualization by medical imaging, as described herein. The indicia is radiographically detectable to indicate orthogonal alignment, as described herein, of cage 12 with tissue such that recess 412 is disposable between a non-aligned orientation and an aligned orientation. For example, when cage 12 is disposed relative to tissue in the non-aligned orientation, visualization of recess 412 is obstructed such that surface 14 is oriented to prevent radiographic visualization of recess 412 through the body of cage 12, as shown in FIG. 14. When cage 12 is rotated relative to tissue to the aligned orientation, surface 14 is oriented to allow radiographic visualization of recess 412 through the body of cage 12, as shown in FIG. 13. In some embodiments, recess 412 is disposed in a medial to lateral orientation. In some embodiments, recess 412 is disposed in an anterior to posterior orientation.

In some embodiments, cage 12 includes any number and configuration of radiopaque markers (such as tantalum pins (not shown)) for visualizing a position and/or alignment of cage 12 using fluoroscopy during insertion, manipulation and implantation thereof. In some embodiments, the markers may be placed obliquely on bullet nose 18, in sidewalls of cage 12 adjacent surfaces 14, 16 and/or in a proximal end of cage 12. In some embodiments, the markers may be placed parallel, oblique to and/or perpendicular to surfaces 14, 16 as required to properly visualize the position of cage 12 relative to surgical pathway P to facilitate placement of cage 12, as described herein.

Cage 12 has a substantially rectangular configuration and includes an inner surface 26. Surface 26 defines lateral openings 30 configured to receive an agent, which may include bone graft (not shown) and/or other materials, as described herein, for employment in a fixation or fusion treatment. Surface 22 and surface 24 each include a plurality of hexagonal openings 31 such that surfaces 22, 24 each define a honeycomb configuration, as shown in FIGS. 1 and 2. Surfaces 22, 24 are configured for disposal of fluids, bone graft and/or bone growth through openings 31. A portion of openings 31 are disposed with one or more of grooves 224, 250, 324, 350 for bone growth therein. In some embodiments, one or more of openings 31 may be alternately shaped, such as, for example, polygonal including triangular, quadrilateral, pentagonal, arcuate walls.

Figure 15:
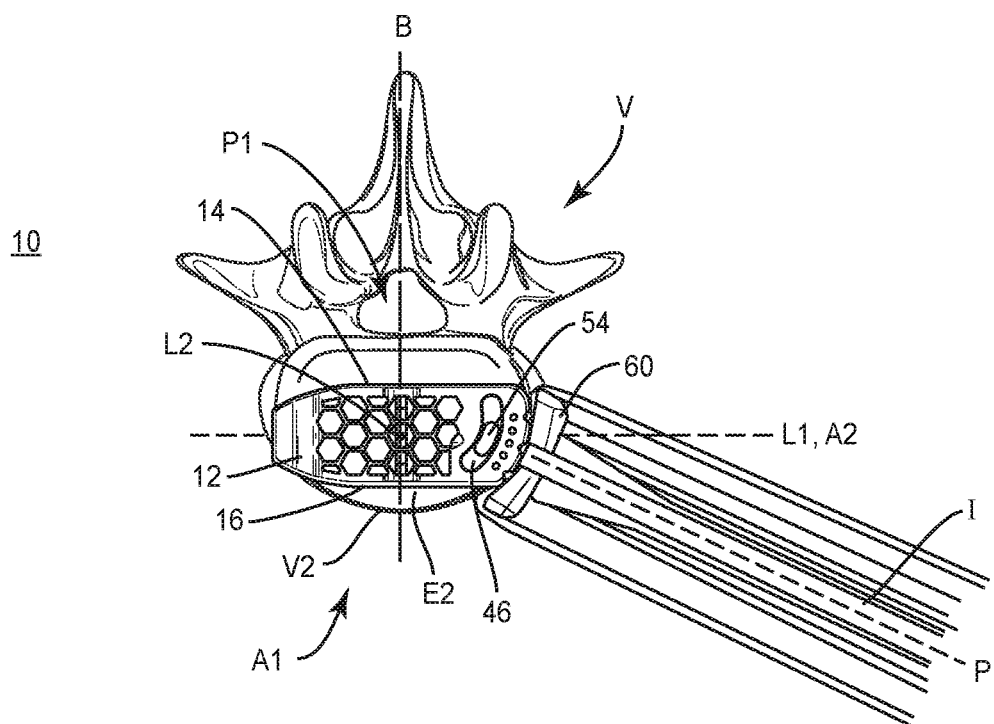
FIG. 15 is an axial view of components of one embodiment of a surgical system in accordance with the principles of the present disclosure disposed with vertebrae.

Cage 12 includes an oblique surface 44 that defines an elongated opening including a track 46. Oblique surface 44 is oriented with cage 12 and in substantial alignment with surgical pathway P (FIG. 15). Track 46 is in open communication with surface 44 to define a track pathway 48 that facilitates translation and/or rotation of a plate connected with cage 12, as described herein. In some embodiments, pathway 48 is arcuate in shape. In some embodiments, track 46 includes a varying radius of curvature. Track 46 includes a limit of a range of translation of an attached implant, such as, for example, a plate 60 relative to cage 12 along track 46 and/or pathway 48, as described herein.

Cage 12 includes a connection mechanism, such as, for example, a slider 54 configured to connect cage 12 with a surgical instrument and/or plate 60. In some embodiments, slider 54 includes a connecting member, such as, for example, a head 92 having an elongated post 94. Head 92 is configured for engagement with and translation along track 46. In some embodiments, post 94 includes a threaded surface configured to facilitate engagement with the surgical instrument. In some embodiments, a dovetail or t-slot sliding attachment mechanism can be utilized. In some embodiments, track 46 and surface 44 are arcuate with each having a single radii. In some embodiments, track 46 and surface 44 have multiple radii.

Slider 54 is slidably engageable with track 46 and/or plate 60 for translation relative to cage 12 along track pathway 48. Slider 54 is movable along track pathway 48 for translation substantially along axis L2 and/or transverse to axis L1. Slider 54 is movable along track pathway 48 for rotation about axis L2 and/or axis L1. In some embodiments, track pathway 48 extends along an arcuate configuration that is substantially concentric with track 46 and/or a lateral surface of cage 12.

Plate 60 includes a portion configured to engage a vertebral level. In some embodiments, a surgical instrument or tool, as described herein, manipulates and/or rotates plate 60 about cage 12 and/or tissue for alignment with selected vertebral tissue, for example, a superior vertebral body such as vertebral level V1 or an inferior vertebral body such as vertebral level V2 for orienting a fastener for fixation of cage 12 and/or plate 60 with the selected vertebral level. In some embodiments, plate 60 may be attached with cage 12 prior to implantation, in vivo or in situ. In some embodiments, plate 60 is removably connected with cage 12.

Spinal implant system 10 includes one or more fasteners (not shown) for attaching plate 60 and/or cage 12 to tissue, as described herein. In some embodiments, the fastener may be engaged with tissue, such as, for example, the bony structures of a vertebral body in various orientations, such as, for example, series, parallel, offset, staggered and/or alternate vertebral levels. In some embodiments, one or more of fasteners may comprise multi-axial screws, sagittal angulation screws, pedicle screws, mono-axial screws, uniplanar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts. In some embodiments, spinal implant system 10 may comprise various surgical instruments, such as, for example, drivers, extenders, reducers, spreaders, distracters, blades, forceps, elevators and drills, which may be alternately sized and dimensioned, and arranged as a kit.

In assembly, operation and use, as shown in FIGS. 15-18, spinal implant system 10, similar to the systems and methods described herein, is employed with a surgical procedure for treatment of a spinal disorder, such as those described herein, affecting a section of a spine of a patient. The components of spinal implant system 10 are employed with a surgical procedure for treatment of a spinal disorder affecting a section of a spine of a patient, for example, to treat the affected section of vertebrae V of a patient utilizing an OLIF or DLIF procedure. Vertebrae V defines a transverse and/or axial plane A2 and bi-lateral axis B.

A retractor (not shown) is disposed in communication with surgical pathway P for spacing tissue. In some embodiments, an annulotomy and/or discectomy is performed with a surgical instrument with x-ray confirmation of the starting point that is central on one or more intervertebral spaces. A probe is passed into the disc space to secure its location. In some embodiments, the oblique angle and lordotic angle of the probe as it enters the disc space is assessed pre-operatively and measured intra-operative using image guidance or using a mechanical or digital protractor. Fluoroscopy, image guidance and/or surgical navigation, as described herein, is used to confirm proper probe alignment into the disc space. In some embodiments, a guide wire is placed through a cannula into the disc space and positioning is confirmed with fluoroscopy. Instruments, such as, for example, a Cobb, mallet, shaver, serrated curettes, rasp, a ring curette, a uterine curette and/or combo tools are utilized to perform a discectomy of the disc space. The instruments enter the patient body obliquely through the retractor and can be turned orthogonally to allow the surgeon to work orthogonally across the disc space. The disc space is distracted until adequate disc space height is obtained.

In some embodiments, a discectomy is performed via surgical pathway P. In some embodiments, trial implants are delivered along surgical pathway P and used to distract one or more intervertebral spaces and apply appropriate tension in the intervertebral space allowing for indirect decompression. In some embodiments, a direct decompression of the disc space is performed by removing a portion of a herniated disc. In some embodiments, the size of cage 12 is selected after trialing and cage 12 is visualized by fluoroscopy and oriented before malleting into the intervertebral space. Trialing is utilized to establish a starting point for cage 12 insertion. In some embodiments, an anterior longitudinal ligament (ALL) release procedure can be performed using an OLIF or a DLIF approach post-discectomy. For example, loosening the ALL can be performed by placing holes or partial cuts in the ALL such that the OLIF surgical pathway is immediately closer to the ALL.

A pilot hole(s) or the like is made in selected vertebra V1 of vertebrae V adjacent an intervertebral space S, via surgical pathway P, for receiving a bone fastener, as described herein. Inserter I is attached with cage 12 and/or plate 60, as described herein. Inserter I delivers cage 12 and plate 60 along surgical pathway P adjacent to a surgical site for implantation adjacent intervertebral space S between vertebrae V1 and V2. In some embodiments, inserter I includes a navigation component to facilitate placement of cage 12 and plate 60 between vertebrae V1, V2. In some embodiments, inserter I includes one or more metallic portions engageable and/or connectable with one or more metallic portions of cage 12 and plate 60. As such, the metal on metal engagement and/or connection of inserter I, cage 12 and/or plate 60 provides more rigidity and control for selected or compatible insertion angulation of inserter I, cage 12 and/or plate 60 relative to a surgical approach, inserter I and/or implant axis. In some embodiments, the metal on metal engagement and/or connection of inserter I, cage 12 and/or plate 60 resists and/or prevents deformation or bending at the inserter I, cage 12 and/or plate 60 interface. For example, during an insertion technique using an OLIF surgical approach, cage 12 may require angulation and/or rotation from an anterior incision to, for example, an L45 disc such that the interface of metallic surfaces of inserter I and cage 12 provide a rigid connection and control for resisting and/or preventing deformation or bending at the interface.

During insertion, inserter I is attached with plate 60 to manipulate plate 60 relative to cage 12. Cage 12 and plate 60 are inserted through the retractor adjacent the surgical site. Anterior surface 16 faces an anterior side of the patient body adjacent anterior portion A1 and posterior surface 14 faces a posterior side of the patient body adjacent posterior portion P1, as described herein. Surface 22 engages endplate tissue of endplate E1 and surface 24 engages endplate tissue of endplate E2.

Inserter I is attached with cage 12 to manipulate cage 12 into orthogonal alignment with bi-lateral axis B such that axis L1 is oriented perpendicular relative to axis B for selective positioning of cage 12 with intervertebral space S. Cage 12 comprises opening 402, which comprises indicia that is radiographically detectable to indicate orthogonal alignment of cage 12 relative to axis B. For example, from a non-aligned orientation, as described herein and shown in FIG. 12, cage 12 is rotated with inserter I relative to endplates E1, E2 and disc space S to an aligned orientation such that surface 400 is oriented to allow radiographic visualization of opening 402 through the body of cage 12, as shown in FIGS. 11 and 15. In some embodiments, from a non-aligned orientation, as described herein and shown in FIG. 14, cage 12 is rotated with inserter I relative to endplates E1, E2 and disc space S to an aligned orientation such that surface 14 is oriented to allow radiographic visualization of recess 412 through the body of cage 12, as shown in FIGS. 13 and 15. In some embodiments, cage 12 can be selectively aligned with endplates E1, E2 and disc space S in alternate orientations relative to axis B, for example, angular orientations and/or offset.

In some embodiments, spinal implant system 10 includes an agent, which may be disposed, packed, coated or layered within, on or about the components and/or surfaces of cage 12. In some embodiments, the agent may include bone growth promoting material, such as, for example, bone graft to enhance fixation of the components and/or surfaces of cage 12 with vertebrae. In some embodiments, the agent may include one or a plurality of therapeutic agents and/or pharmacological agents for release, including sustained release, to treat, for example, pain, inflammation and degeneration.

After positioning of cage 12 with endplates E1, E2 and disc space S, plate 60 is rotated into position relative to vertebrae V1, V2. Translation and rotation of plate 60 allows selective manipulation of plate 60 to facilitate plate 60 positioning relative to vertebrae V1, V2. In some embodiments, inserter I or other surgical instruments, as described herein, engages plate 60 to rotate plate 60, in a clockwise or counter-clockwise direction, for alignment and orienting a fastener for fixation of cage 12 and/or plate 60 with vertebral levels V1, V2.

Fasteners are aligned with tissue, and inserted along inserter I via a driver (not shown). Fasteners engage vertebra V1 and/or vertebra V2. The driver is configured to drive, torque, insert or otherwise fasten fasteners with vertebrae V1, V2 adjacent intervertebral space S. In some embodiments, the driver may include surgical navigation components, as described herein, to establish a pathway for the fastener that is substantially concurrent with and/or parallel to the surgical approach angle. In some embodiments, plate 60 is fixed with fasteners at an oblique angle relative to cage 12. In some embodiments, plate 60 is fixed with fasteners laterally with cage 12. Upon completion of a procedure, as described herein, the surgical instruments, assemblies and non-implanted components of spinal implant system 10 are removed and the incision(s) are closed.

Upon completion of the procedure, as described above, identification, confirmation and/or assessment of regeneration of natural bone tissue and/or successful bone grafting within, on or about the surfaces of cage 12 can be performed via medical imaging in a subsequent procedure and/or examination of the surgical site to assess treatment. For example, medical imaging, as described herein, is employed to radiographically detect the indicia of grooves 224, 250, 324, 350, as described herein, for detecting bone growth BG in and through grooves 224, 250, 324, 350, as shown in FIG. 18. The indicia of grooves 224, 250, 324, 350 provide visualization to confirm and/or assess the rate, amount and/or progression of bone growth between endplates E1, E2 and surfaces 22, 24. As such, the indicia of grooves 224, 250, 324, 350 provide a visual assessment of fusion of vertebral levels V1, V2 with cage 12, as well as the progression of bone growth BG and/or migration into grooves 224, 250, 324, 350.

Figure 19:
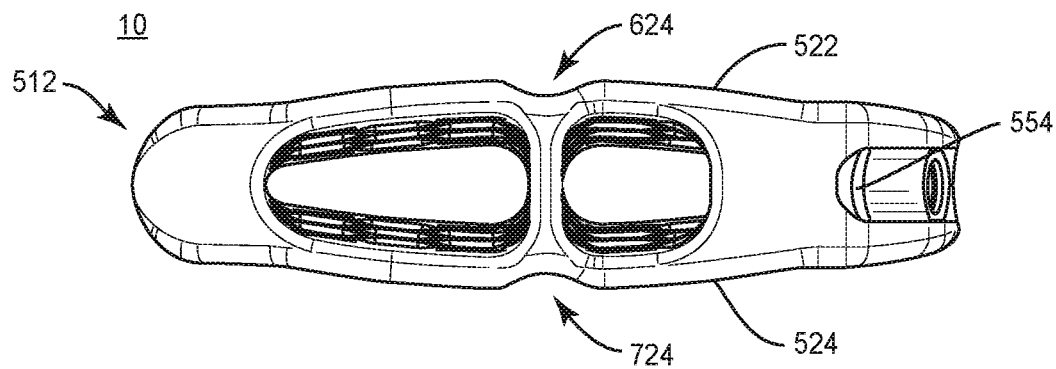
FIG. 19 is a front view of components of one embodiment of a surgical system in accordance with the principles of the present disclosure.
Figure 20:
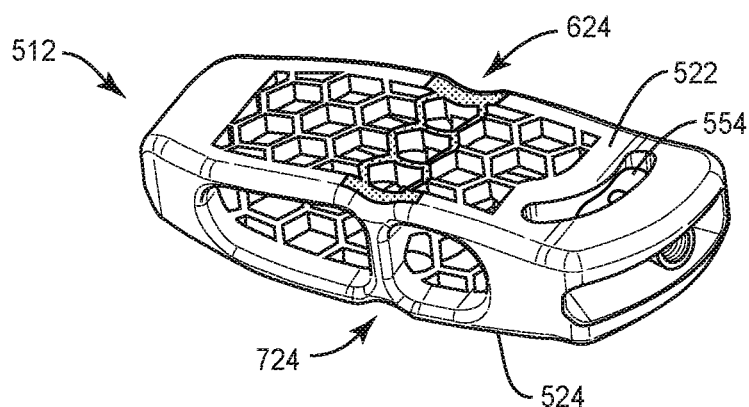
FIG. 20 is a perspective view of the components shown in FIG. 19.
Figure 21:
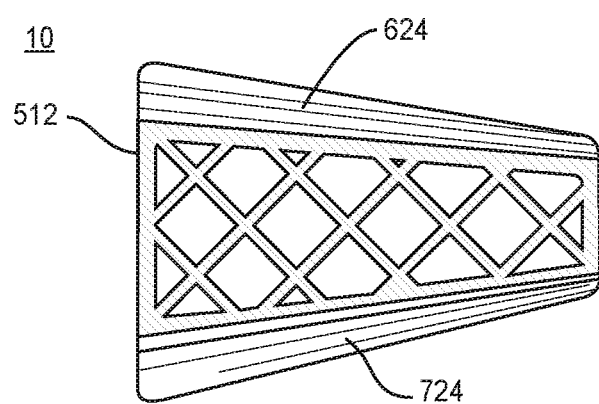
FIG. 21 is a cross section view of the components shown in FIG. 19.

In one embodiment, as shown in FIGS. 19-21, spinal implant system 10, similar to the systems and methods described herein, includes a cage 512, similar to cage 12 described herein. Cage 512 includes a surface 522, similar to surface 22 described herein. Surface 522 defines a groove 624, similar to groove 224 described herein. Groove 624 extends in an anterior to posterior orientation along surface 522. Groove 624 extends along surface 522 such that all or only a portion of groove 624 is disposed in a parallel orientation relative to endplate E1, endplate E2 and/or a selected lordosis of vertebrae V (FIGS. 15-18). The portion of surface 522 that defines groove 624 comprises indicia that facilitates detecting bone growth in and/or through groove 624 and surface 522 via medical imaging, as described herein. The indicia is configured to facilitate visualization of a progression of bone growth into groove 624, for example, during fusion. In some embodiments, surface 522 may define one or a plurality of grooves 624, which may be disposed at alternate relative orientations, as described herein.

Cage 512 includes a surface 524, similar to surface 24 described herein. Surface 524 defines a groove 724, similar to groove 224 described herein. Groove 724 extends in an anterior to posterior orientation along surface 524. Groove 724 extends along surface 524 such that all or only a portion of groove 724 is disposed in a parallel orientation relative to endplate E1, endplate E2 and/or a selected lordosis of vertebrae V (FIGS. 15-18). The portion of surface 524 that defines groove 724 comprises indicia that facilitates detecting bone growth in and/or through groove 724 and surface 524 via medical imaging, as described herein. The indicia is configured to facilitate visualization of a progression of bone growth into groove 724, for example, during fusion. In some embodiments, groove 724 may be disposed at alternate orientations, relative to groove 624, as described herein. In some embodiments, surface 524 may define one or a plurality of grooves 724, which may be disposed at alternate relative orientations, as described herein. In some embodiments, cage 512 includes a slider 554, similar to slider 54 described herein, configured to connect cage 512 with a surgical instrument and/or plate 60.

Figure 22:
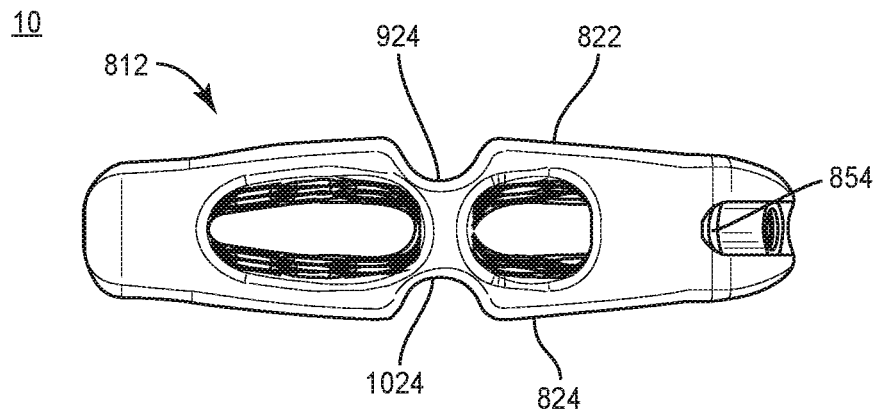
FIG. 22 is a side view of components of one embodiment of a surgical system in accordance with the principles of the present disclosure.
Figure 23:
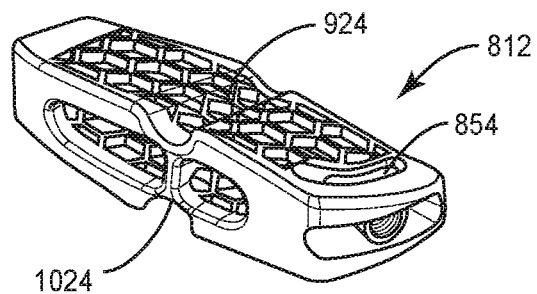
FIG. 23 is a perspective view of the components shown in FIG. 22.
Figure 24:
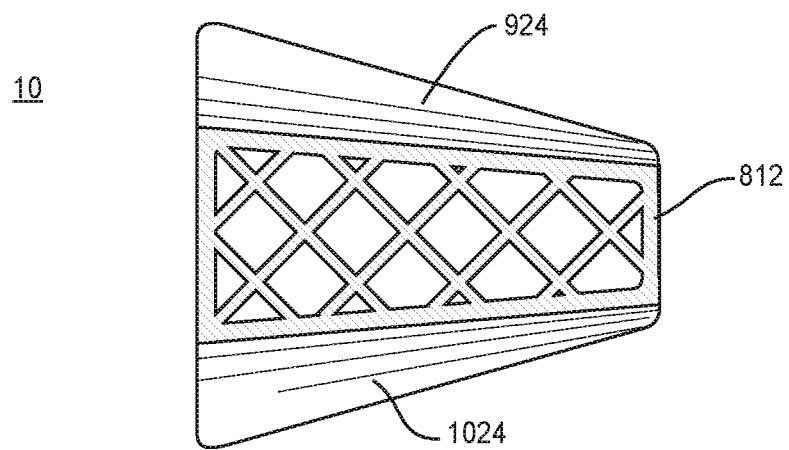
FIG. 24 is a cross section view of the components shown in FIG. 22.

In one embodiment, as shown in FIGS. 22-24, spinal implant system 10, similar to the systems and methods described herein, includes a cage 812, similar to cage 12 described herein. Cage 812 includes a surface 822, similar to surface 22 described herein. Surface 822 defines a groove 924, similar to groove 224 described herein. Groove 924 extends in an anterior to posterior orientation along surface 822. Groove 924 extends along surface 822 such that all or only a portion of groove 924 is disposed at a selected angular orientation relative to endplate E1, endplate E2, a selected lordosis of vertebrae V, bi-lateral axis B and/or an axial plane of vertebrae V (FIGS. 15-18). For example, all or only a portion of groove 924 can be disposed at a selected angular orientation between endplates E1, E2 and an axial plane of vertebrae V. The portion of surface 822 that defines groove 924 comprises indicia that facilitates detecting bone growth in and/or through groove 924 and surface 822 via medical imaging, as described herein. The indicia is configured to facilitate visualization of a progression of bone growth into groove 924, for example, during fusion. In some embodiments, surface 822 may define one or a plurality of grooves 924, which may be disposed at alternate relative orientations, as described herein.

Cage 812 includes a surface 824, similar to surface 24 described herein. Surface 824 defines a groove 1024, similar to groove 224 described herein. Groove 1024 extends in an anterior to posterior orientation along surface 824. Groove 1024 extends along surface 824 such that all or only a portion of groove 1024 is disposed at a selected angular orientation relative to endplate E1, endplate E2, a selected lordosis of vertebrae V, bi-lateral axis B and/or an axial plane of vertebrae V (FIGS. 15-18). For example, all or only a portion of groove 1024 can be disposed at a selected angular orientation between endplates E1, E2 and an axial plane of vertebrae V. The portion of surface 824 that defines groove 1024 comprises indicia that facilitates detecting bone growth in and/or through groove 1024 and surface 824 via medical imaging, as described herein. The indicia is configured to facilitate visualization of a progression of bone growth into groove 1024, for example, during fusion. In some embodiments, groove 1024 may be disposed at alternate orientations, relative to groove 924, as described herein. In some embodiments, surface 824 may define one or a plurality of grooves 1024, which may be disposed at alternate relative orientations, as described herein. In some embodiments, cage 812 includes a slider 854, similar to slider 54 described herein, configured to connect cage 812 with a surgical instrument and/or plate 60.

Figure 25:
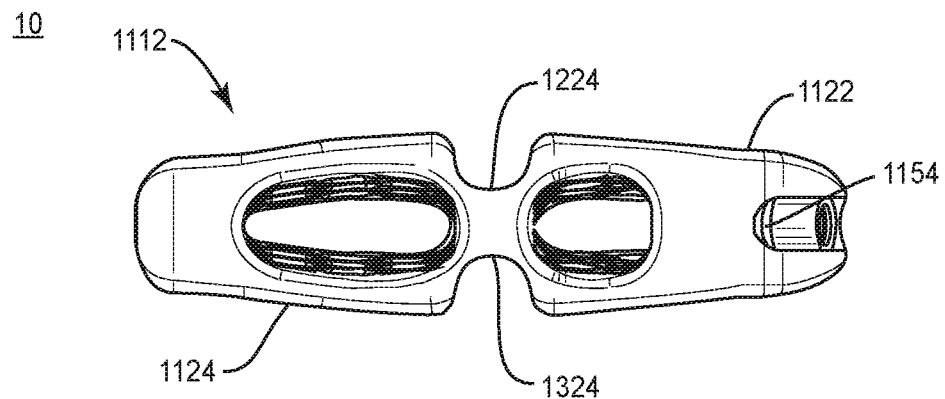
FIG. 25 is a side view of components of one embodiment of a surgical system in accordance with the principles of the present disclosure.
Figure 26:
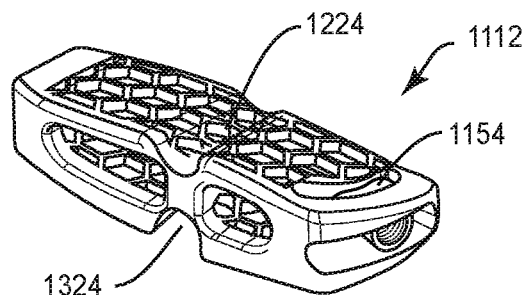
FIG. 26 is a perspective view of the components shown in FIG. 25.
Figure 27:
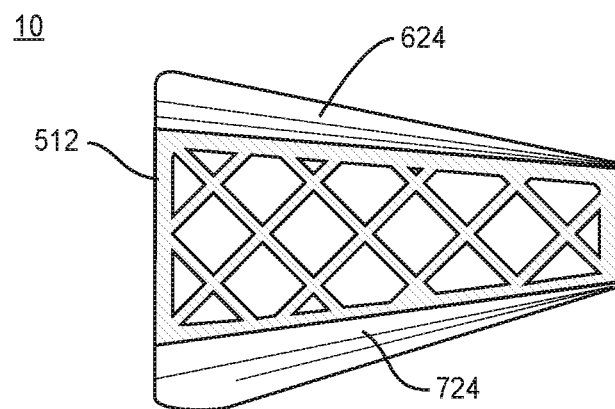
FIG. 27 is a cross section view of the components shown in FIG. 25.

In one embodiment, as shown in FIGS. 25-27, spinal implant system 10, similar to the systems and methods described herein, includes a cage 1112, similar to cage 12 described herein. Cage 1112 includes a surface 1122, similar to surface 22 described herein. Surface 1122 defines a groove 1224, similar to groove 224 described herein. Groove 1224 extends in an anterior to posterior orientation along surface 1122. Groove 1224 extends along surface 1122 such that all or only a portion of groove 1224 is disposed in a parallel orientation relative to bi-lateral axis B and/or an axial plane of vertebrae V (FIGS. 15-18). The portion of surface 1122 that defines groove 1224 comprises indicia that facilitates detecting bone growth in and/or through groove 1224 and surface 1122 via medical imaging, as described herein. The indicia is configured to facilitate visualization of a progression of bone growth into groove 1224, for example, during fusion. In some embodiments, surface 1122 may define one or a plurality of grooves 1224, which may be disposed at alternate relative orientations, as described herein.

Cage 1112 includes a surface 1124, similar to surface 24 described herein. Surface 1124 defines a groove 1324, similar to groove 224 described herein. Groove 1324 extends in an anterior to posterior orientation along surface 1124. Groove 1324 extends along surface 1124 such that all or only a portion of groove 1324 is disposed in a parallel orientation relative to bi-lateral axis B and/or an axial plane of vertebrae V (FIGS. 15-18). The portion of surface 1124 that defines groove 1324 comprises indicia that facilitates detecting bone growth in and/or through groove 1324 and surface 1124 via medical imaging, as described herein. The indicia is configured to facilitate visualization of a progression of bone growth into groove 1324, for example, during fusion. In some embodiments, groove 1324 may be disposed at alternate orientations, relative to groove 1224, as described herein. In some embodiments, surface 1124 may define one or a plurality of grooves 1324, which may be disposed at alternate relative orientations, as described herein. In some embodiments, cage 1112 includes a slider 1154, similar to slider 54 described herein, configured to connect cage 1112 with a surgical instrument and/or plate 60.

Figure 28:
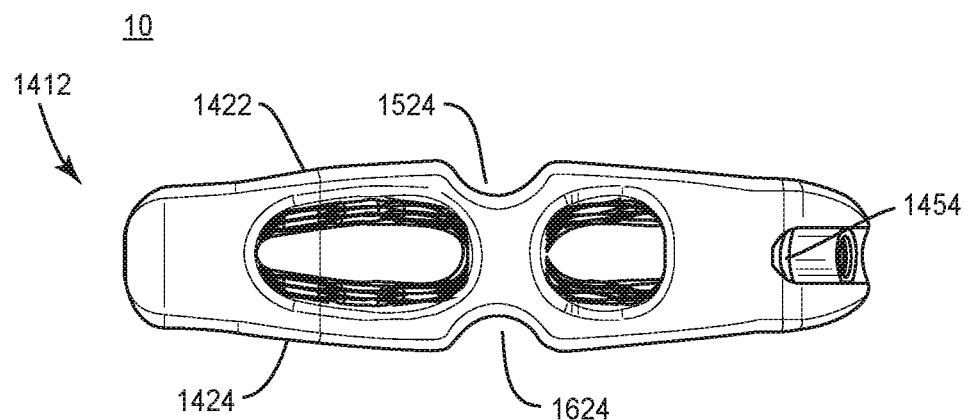
FIG. 28 is a side view of components of one embodiment of a surgical system in accordance with the principles of the present disclosure.
Figure 29:
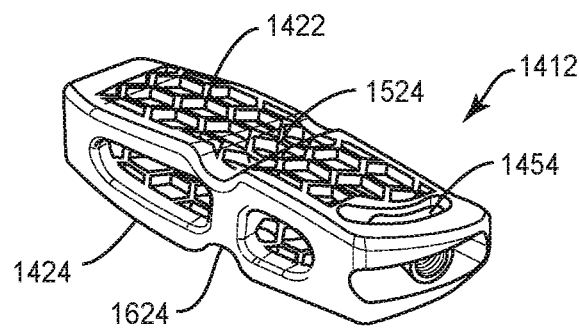
FIG. 29 is a perspective view of the components shown in FIG. 28.
Figure 30:
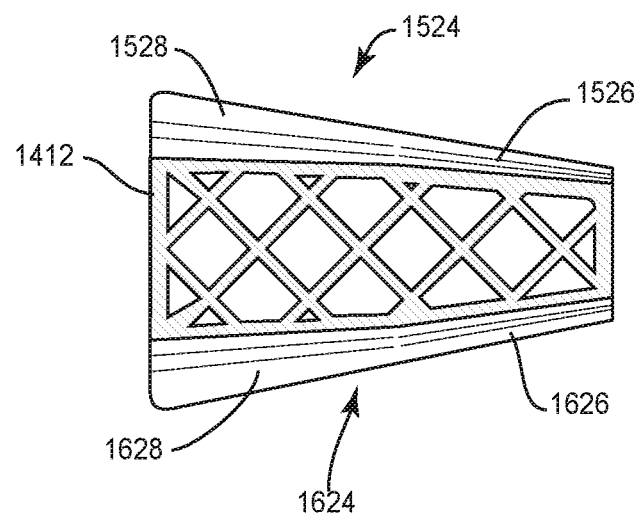
FIG. 30 is a cross section view of the components shown in FIG. 28.

In one embodiment, as shown in FIGS. 28-30, spinal implant system 10, similar to the systems and methods described herein, includes a cage 1412, similar to cage 12 described herein. Cage 1412 includes a surface 1422, similar to surface 22 described herein. Surface 1422 defines a groove 1524, similar to groove 224 described herein. Groove 1524 extends in an anterior to posterior orientation along surface 1422 and includes a posterior portion 1526 and an anterior portion 1528. In some embodiments, portions 1526, 1528 are equal such that posterior portion 1526 comprises a posterior half and anterior portion 1528 comprises an anterior half.

Groove 1524 extends along surface 1422 such that posterior portion 1526 is disposed in a parallel orientation relative to endplates E1, E2 and anterior portion 1528 is disposed in a parallel orientation relative to bi-lateral axis B and/or an axial plane of vertebrae V (FIGS. 15-18). The portion of surface 1422 that defines groove 1524 comprises indicia that facilitates detecting bone growth in and/or through groove 1524 and surface 1422 via medical imaging, as described herein. The indicia is configured to facilitate visualization of a progression of bone growth into groove 1524, for example, during fusion. In some embodiments, surface 1422 may define one or a plurality of grooves 1524, which may be disposed at alternate relative orientations, as described herein.

Cage 1412 includes a surface 1424, similar to surface 24 described herein. Surface 1424 defines a groove 1624, similar to groove 224 described herein. Groove 1624 extends in an anterior to posterior orientation along surface 1424 and includes a posterior portion 1626 and an anterior portion 1628. In some embodiments, portions 1626, 1628 are equal such that posterior portion 1626 comprises a posterior half and anterior portion 1628 comprises an anterior half.

Groove 1624 extends along surface 1424 such that posterior portion 1626 is disposed in a parallel orientation relative to endplates E1, E2 and anterior portion 1628 is disposed in a parallel orientation relative to bi-lateral axis B and/or an axial plane of vertebrae V (FIGS. 15-18). The portion of surface 1424 that defines groove 1624 comprises indicia that facilitates detecting bone growth in and/or through groove 1624 and surface 1424 via medical imaging, as described herein. The indicia is configured to facilitate visualization of a progression of bone growth into groove 1624, for example, during fusion. In some embodiments, groove 1624 may be disposed at alternate orientations, relative to groove 1524, as described herein. In some embodiments, surface 1424 may define one or a plurality of grooves 1624, which may be disposed at alternate relative orientations, as described herein. In some embodiments, cage 1412 includes a slider 1454, similar to slider 54 described herein, configured to connect cage 1412 with a surgical instrument and/or plate 60.

In one embodiment, as shown in FIGS. 31-36, spinal implant system 10, similar to the systems and methods described herein, includes a cage 1712, similar to cage 12 described herein. Cage 1712 includes a surface 1722, similar to surface 22 described herein. Surface 1722 defines a groove 1824, similar to groove 224 described herein. Groove 1824 extends in an anterior to posterior orientation along surface 1722. Groove 1824 extends along surface 1722 such that all or only a portion of groove 1824 is disposed in a parallel orientation relative to endplate E1, endplate E2 and/or a selected lordosis of vertebrae V (FIGS. 15-18). The portion of surface 1722 that defines groove 1824 comprises indicia that facilitates detecting bone growth in and/or through groove 1824 and surface 1722 via medical imaging, as described herein. The indicia is configured to facilitate visualization of a progression of bone growth into groove 1824, for example, during fusion. In some embodiments, surface 1722 may define one or a plurality of grooves 1824, which may be disposed at alternate relative orientations, as described herein.

Figure 34:
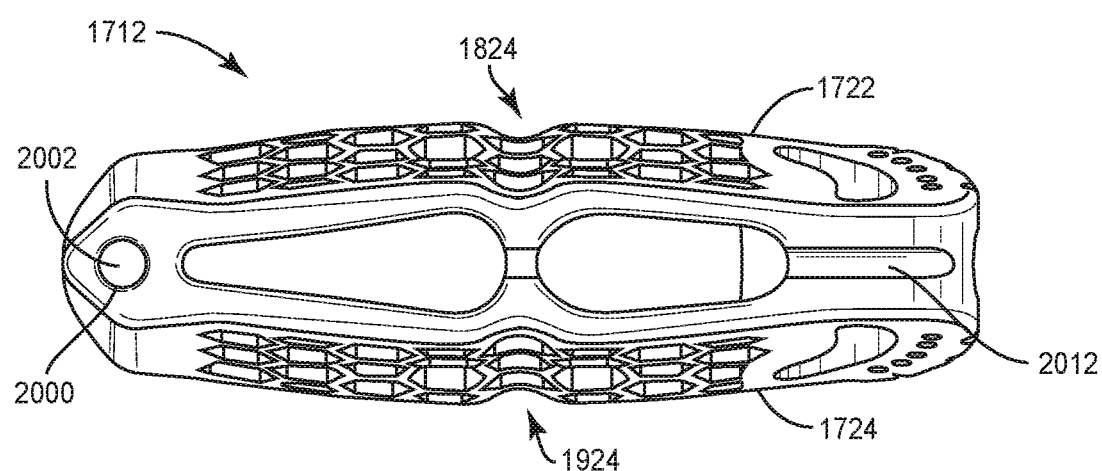
FIG. 34 is a side view of the components shown in FIG. 31.

In some embodiments, surface 1722 defines a groove 1850, as shown in FIG. 34, similar to groove 250 described herein. Groove 1850 extends in a medial to lateral orientation along surface 1722, as described herein. Groove 1850 extends transverse to groove 1824 to intersect and communicate therewith. The portion of surface 1722 that defines groove 1850 comprises indicia that facilitates detecting bone growth in and/or through groove 1850 and surface 1722 via medical imaging, as described herein.

Cage 1712 includes a surface 1724, similar to surface 24 described herein. Surface 1724 defines a groove 1924, similar to groove 224 described herein. Groove 1924 extends in an anterior to posterior orientation along surface 1724. Groove 1924 extends along surface 1724 such that all or only a portion of groove 1924 is disposed in a parallel orientation relative to endplate E1, endplate E2 and/or a selected lordosis of vertebrae V, as described herein. The portion of surface 1724 that defines groove 1924 comprises indicia that facilitates detecting bone growth in and/or through groove 1924 and surface 1724 via medical imaging, as described herein. The indicia is configured to facilitate visualization of a progression of bone growth into groove 1924, for example, during fusion. In some embodiments, groove 1924 may be disposed at alternate orientations, relative to groove 1824, as described herein. In some embodiments, surface 1724 may define one or a plurality of grooves 1924, which may be disposed at alternate relative orientations, as described herein.

Surface 1724 defines a groove 1950, as shown in FIG. 34, similar to groove 350 described herein. Groove 1950 extends in a medial to lateral orientation, as described herein. Groove 1950 extends transverse to groove 1924 to intersect and communicate therewith. The portion of surface 1724 that defines groove 1950 comprises indicia that facilitates detecting bone growth in and/or through groove 1950 and surface 1724 via medical imaging, as described herein.

Figure 31:
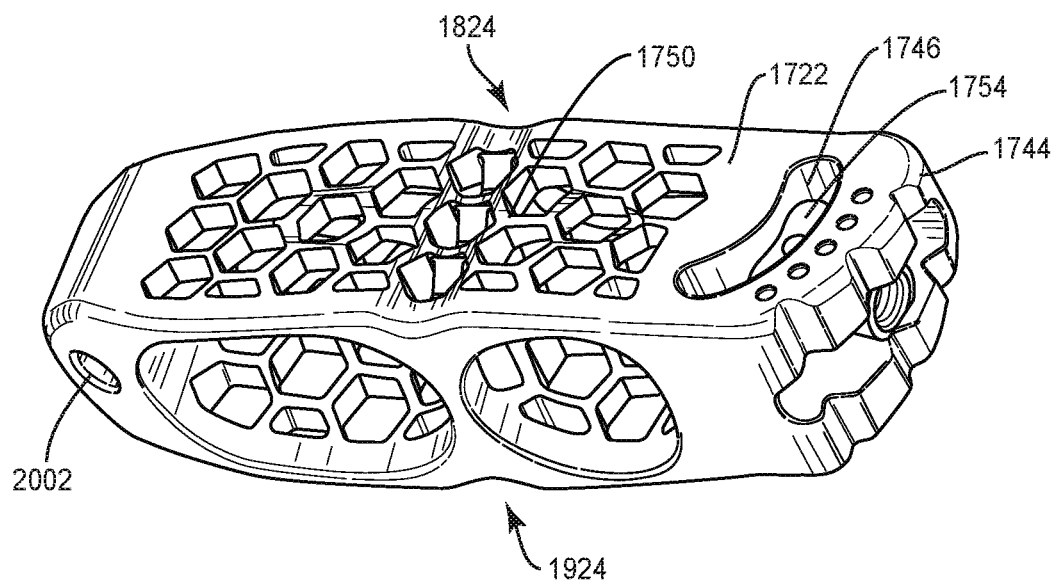
FIG. 31 is a perspective view of components of one embodiment of a surgical system in accordance with the principles of the present disclosure.
Figure 32:
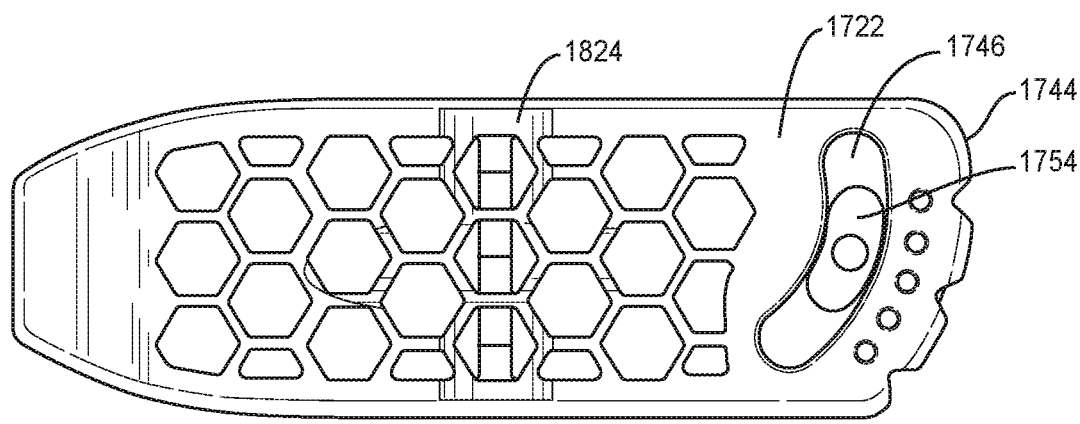
FIG. 32 is a plan view of the components shown in FIG. 31.
Figure 33:
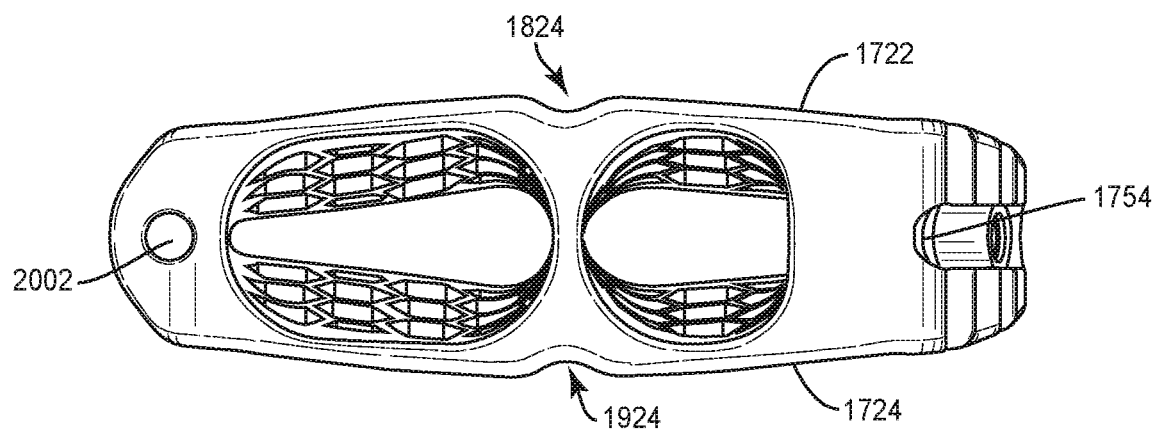
FIG. 33 is a side view of the components shown in FIG. 31.

Cage 1712 includes a surface 2000 that defines an opening 2002, as shown in FIGS. 31 and 33 and similar to opening 402 as described herein. Surface 2000 includes indicia, similar to that described herein, for visualization by medical imaging, as described herein. The indicia is radiographically detectable to indicate orthogonal alignment of cage 1712 relative to a bi-lateral axis of vertebrae, endplates and/or an intervertebral disc space, such that opening 2002 is disposable between a non-aligned orientation and an aligned orientation, as described herein.

Figure 35:
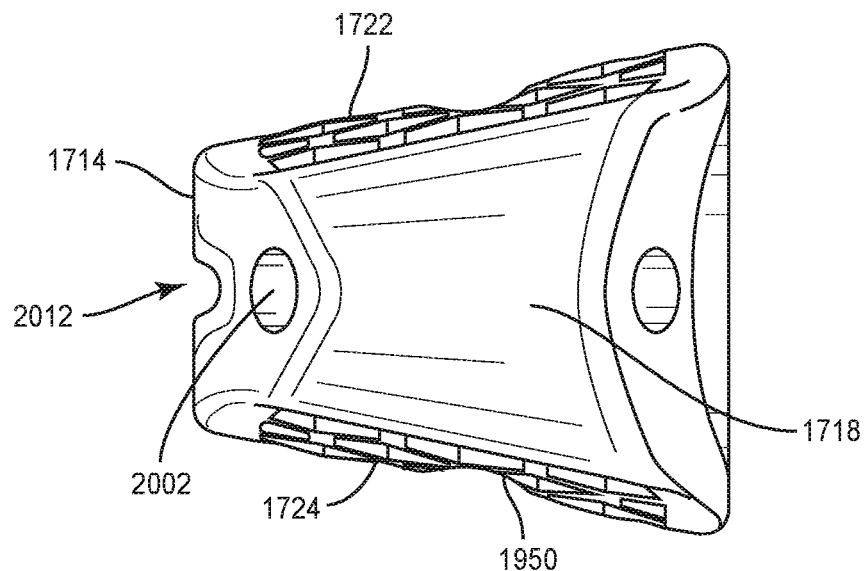
FIG. 35 is a side view of the components shown in FIG. 31.
Figure 36:
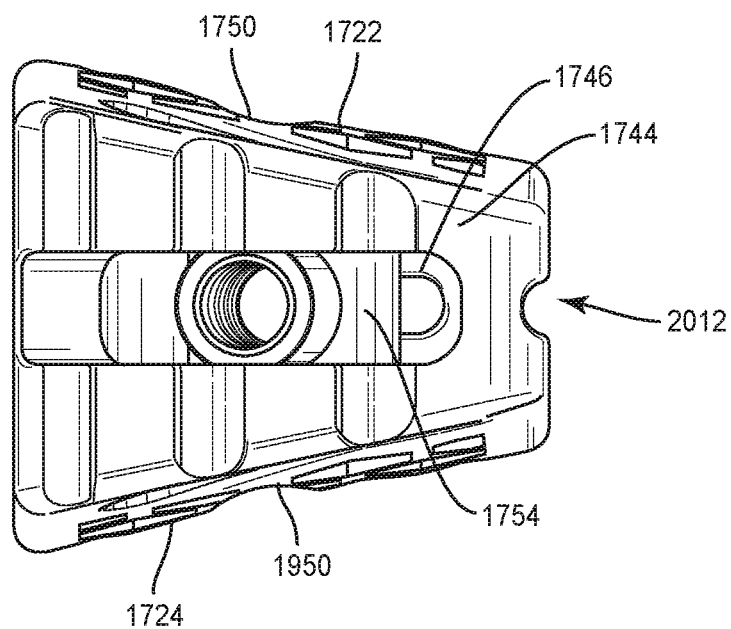
FIG. 36 is a side view of the components shown in FIG. 31.

In some embodiments, a surface 1714 defines a recess 2012, as shown in FIGS. 35 and 36. Recess 2012 extends between a nose 1718 and a surface 1744, as described herein. Surface 1714 includes indicia, similar to the indicia described herein, for visualization by medical imaging, as described herein. The indicia is radiographically detectable to indicate orthogonal alignment, as described herein, of cage 1712 with tissue such that recess 2012 is disposable between a non-aligned orientation and an aligned orientation, as described herein.

Cage 1712 includes oblique surface 1744 that defines an elongated opening including a track 1746, similar to track 46 described herein. Cage 1712 includes a slider 1754, similar to slider 54, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An interbody implant comprising:
an implant body extending along a longitudinal axis between opposite first and second ends, the implant body including an anterior surface and an opposite posterior surface, the anterior and posterior surfaces each extending from the first end to the second end, the implant body including a substantially planar first vertebral engaging surface and an opposite second vertebral engaging surface, the first and second vertebral engaging surfaces each extending from the first end to the second end and from the anterior surface to the posterior surface, the implant body including an opening extending through the anterior and posterior surfaces, the first vertebral engaging surface defining only one groove extending along the longitudinal axis and only one groove extending transverse to the longitudinal axis, the groove extending transverse to the longitudinal axis being a first groove and the groove extending along the longitudinal axis being a second groove, the grooves each extending into the first vertebral engaging surface without extending through the second vertebral engaging surface, the second groove extending transverse to the first groove to intersect and communicate with the first groove, the grooves each being configured for disposal of bone growth detectable via medical imaging,
wherein the implant body is configured to be manipulated between a non-aligned orientation in which visualization of the opening is obstructed by a surface of the implant body that prevents radiographic visualization of the opening and an aligned orientation in which the surface is oriented to allow radiographic visualization of the opening.

2. An interbody implant as recited in claim 1, wherein the opening comprises radiographic visual indicia of disposal of the interbody implant in a selected alignment with tissue.

3. An interbody implant as recited in claim 1, wherein the implant body defines a recess extending into the posterior surface, the recess extending parallel to the anterior surface such that the recess is radiographically detectable in the aligned orientation and the recess is radiographically non-detectable in the non-aligned orientation.

4. An interbody implant as recited in claim 1, wherein one or more of the surfaces include a honeycomb configuration.

5. An interbody implant as recited in claim 1, wherein the first groove has a linear configuration and is disposed in an anterior to posterior orientation relative to the vertebral engaging surfaces.

6. An interbody implant as recited in claim 1, wherein the second groove has a linear configuration and is disposed in a lateral orientation relative to the vertebral engaging surfaces.

7. An interbody implant as recited in claim 1, further comprising a plate connectable with the implant body via a coupling member and defining a single opening oriented to implant a fastener with tissue.

8. An interbody implant as recited in claim 1, wherein the first end defines a bullet nose.

9. An interbody implant as recited in claim 1, wherein:
the implant body includes an aperture in the second end and a track extending through the first vertebral engaging surface such that the track is in communication with the aperture; and
the implant comprises a slider having a head positioned in the track and a post positioned in the aperture.

10. An interbody implant as recited in claim 9, wherein the head is configured for engagement and translation along the track and the post is fixed to the head and comprises a threaded surface configured to facilitate engagement with a surgical instrument.

11. An interbody implant as recited in claim 1, wherein the first groove extends continuously from the anterior surface to the posterior surface.

12. An interbody implant as recited in claim 1, wherein the first groove comprises a first end extending through the anterior surface and an opposite second end extending through the posterior surface.

13. An interbody implant as recited in claim 1, wherein the opening extends parallel to the first groove.

14. An interbody implant as recited in claim 1, wherein the first vertebral engaging surface is free of any teeth that extend outwardly from the first vertebral engaging surface.

15. An interbody implant as recited in claim 1, wherein the first vertebral engaging surface includes an area that extends from the second groove to an end surface of the first end and from the posterior surface to the anterior surface, the area being substantially planar.

16. An interbody implant as recited in claim 1, wherein the first vertebral engaging surface includes an area that extends from the second groove to an end surface of the second end and from the posterior surface to the anterior surface, the area being substantially planar.

17. An interbody implant as recited in claim 1, wherein the first vertebral engaging surface includes a first area that extends from the second groove to an end surface of the first end and from the posterior surface to the anterior surface, the area being substantially planar, the first vertebral engaging surface including a second area that extends from the second groove to an end surface of the second end and from the posterior surface to the anterior surface, the first and second areas each being substantially planar.

18. An interbody implant comprising:
an implant body extending along a longitudinal axis between opposite first and second ends, the implant body including an anterior surface and an opposite posterior surface, the anterior and posterior surfaces each extending from the first end to the second end, the implant body including a substantially planar superior vertebral engaging surface and an opposite inferior vertebral engaging surface, the superior and inferior vertebral engaging surfaces each extending from the first end to the second end and from the anterior surface to the posterior surface, the implant body including an opening extending continuously through the anterior and posterior surfaces,
the superior vertebral engaging surface defining only one groove extending along the longitudinal axis and only one groove extending transverse to the longitudinal axis, the groove extending along the longitudinal axis being a first groove and the groove extending transverse to the longitudinal axis being a second groove, the first and second grooves each extending into the superior surface, the first groove having a linear configuration, the first groove being disposed in an anterior to posterior orientation relative to the superior surface, the second groove having a linear configuration and being disposed in a lateral orientation relative to the superior surface, the second groove extending transverse to the first groove to intersect and communicate with the first groove, and the inferior surface defining a third groove having a linear configuration and being disposed in an anterior to posterior orientation relative to the inferior surface, the inferior surface defining a fourth groove having a linear configuration and being disposed in a lateral orientation relative to the superior surface, the fourth groove extending transverse to the third groove to intersect and communicate with the third groove, the grooves being configured for disposal of bone growth detectable via medical imaging, wherein the implant body is configured to be manipulated between a non-aligned orientation in which visualization of the opening is obstructed by a surface of the implant body that prevents radiographic visualization of the opening and an aligned orientation in which the surface is oriented to allow radiographic visualization of the opening.

19. An interbody implant as recited in claim 18, wherein the implant body comprises a recess extending into the posterior surface, the recess extending parallel to the anterior surface such that the recess is radiographically detectable in the aligned orientation and the recess is radiographically non-detectable in the non-aligned orientation.

20. An interbody implant comprising:
an implant body extending along a longitudinal axis between opposite first and second ends, the implant body including an anterior surface and an opposite posterior surface, the anterior and posterior surfaces each extending from the first end to the second end, the implant body including a substantially planar first vertebral engaging surface and an opposite second vertebral engaging surface, the first and second vertebral engaging surface each extending from the first end to the second end and from the anterior surface to the posterior surface, the implant body including an opening extending through the anterior and posterior surfaces and a recess extending into the posterior surface, and the first vertebral engaging surface defining only one trough extending along the longitudinal axis and only one trough extending transverse to the longitudinal axis, the trough extending along the longitudinal axis being a first trough and the trough extending transverse to the longitudinal axis being a second trough, the troughs each extending into the first vertebral engaging surface, the troughs being configured for disposal of bone growth and detectable to provide radiographic visual indicia, the second trough extending transverse to the first trough to intersect and communicate with the first trough, wherein the implant body is configured to be manipulated between a non-aligned orientation in which visualization of the opening is obstructed by a surface of the implant body that prevents radiographic visualization of the opening and an aligned orientation in which the surface is oriented to allow radiographic visualization of the opening, and wherein the recess extends parallel to the anterior surface such that the recess is radiographically detectable in the aligned orientation and the recess is radiographically non-detectable in the non-aligned orientation.

21. A method for treating a spine, the method comprising the steps of:
connecting a surgical instrument with an implant body adjacent a cavity of the implant body, the implant body extending between opposite first and second ends, the implant body including opposite anterior and posterior surfaces, the anterior and posterior surfaces each extending from the first end to the second end, the implant body including opposite first and second vertebral engaging surfaces, the first and second vertebral engaging surfaces each extending from the first end to the second end and from the anterior surface to the posterior surface, the implant body including an opening extending through the anterior and posterior surfaces and a recess extending into the posterior surface;

disposing the implant body between a first vertebral surface and a second vertebral surface of a subject body;

manipulating the implant body between a non-aligned orientation such that visualization of the opening is obstructed by a surface of the implant body that prevents radiographic visualization of the opening and an aligned orientation such that the surface is oriented to allow radiographic visualization of the opening; and manipulating the implant body such that recess is detectable to indicate orthogonal alignment of the implant body with the vertebral surfaces.

\* \* \* \* \*